US012805950B2

(12) United States Patent
Morard et al.

(10) Patent No.: US 12,805,950 B2
(45) Date of Patent: *Nov. 24, 2026

(54) SYSTEMS AND METHODS FOR PERFORMING MINIMALLY INVASIVE SPINAL SURGERY WITH A ROBOTIC SURGICAL SYSTEM USING A PERCUTANEOUS TECHNIQUE

(71) Applicant: KB MEDICAL SA, Audubon, PA (US)

(72) Inventors: Marc Morard, Lausanne (CH); Kristof van Dommelen, Lausanne (CH)

(73) Assignee: Globus Medical Inc., Audubon, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/788,713

(22) Filed: Jul. 30, 2024

(65) Prior Publication Data

US 2024/0382275 A1 Nov. 21, 2024

Related U.S. Application Data

(63) Continuation of application No. 17/588,992, filed on Jan. 31, 2022, now Pat. No. 12,076,095, which is a (Continued)

(51) Int. Cl.

*A61B 34/30* (2016.01)
*A61B 17/16* (2006.01)

(Continued)

(52) U.S. Cl.

CPC .......... *A61B 34/30* (2016.02); *A61B 17/1671* (2013.01); *A61B 17/17* (2013.01); *A61B 17/1703* (2013.01); *A61B 17/1757* (2013.01); *A61B 17/70* (2013.01); *A61B 34/10* (2016.02); *A61B 34/20* (2016.02); *A61B 34/25* (2016.02);

(Continued)

(58) Field of Classification Search

CPC ............ A61B 34/20; A61B 2034/2046; A61B 2034/2059; A61B 2034/2068; A61B 2034/252; A61B 2034/254; A61B 2034/303

See application file for complete search history.

(56) References Cited

U.S. PATENT DOCUMENTS 4,150,293 A 4/1979 Franke
5,246,010 A 9/1993 Gazzara et al.

(Continued)

OTHER PUBLICATIONS

US 8,231,638 B2, 07/2012, Swarup et al. (withdrawn)

*Primary Examiner* — Anu Ramana

(57) ABSTRACT

Described herein are systems, apparatus, and methods for precise placement and guidance of tools during surgery, particularly spinal surgery, using minimally invasive surgical techniques. Several minimally invasive approaches to spinal surgeries were conceived, percutaneous technique being one of them. This procedures looks to establish a skin opening as small as possible by accessing inner organs via needle-puncture of the skin. The percutaneous technique is used in conjunction with a robotic surgical system to further enhance advantages of manual percutaneous techniques by improving precision, usability and/or shortening surgery time by removal of redundant steps.

13 Claims, 16 Drawing Sheets

Related U.S. Application Data continuation of application No. 16/720,187, filed on Dec. 19, 2019, now Pat. No. 11,266,470, which is a continuation of application No. 15/047,277, filed on Feb. 18, 2016, now Pat. No. 10,555,782.

(60) Provisional application No. 62/117,919, filed on Feb. 18, 2015.

(51) Int. Cl.

*A61B 17/17* (2006.01)
*A61B 17/70* (2006.01)
*A61B 34/00* (2016.01)
*A61B 34/10* (2016.01)
*A61B 34/20* (2016.01)
*A61B 90/11* (2016.01)
*B25J 9/16* (2006.01)

(52) U.S. Cl.

CPC ............ *A61B 90/11* (2016.02); *B25J 9/1694* (2013.01); *A61B 2034/107* (2016.02); *A61B 2034/2048* (2016.02); *A61B 2034/254* (2016.02); *A61B 2034/256* (2016.02)

(56) References Cited

U.S. PATENT DOCUMENTS 5,354,314 A 10/1994 Hardy et al.
5,397,323 A 3/1995 Taylor et al.
5,598,453 A 1/1997 Baba et al.
5,772,594 A 6/1998 Barrick
5,791,908 A 8/1998 Gillio
5,820,559 A 10/1998 Ng et al.
5,825,982 A 10/1998 Wright et al.
5,887,121 A 3/1999 Funda et al.
5,911,449 A 6/1999 Daniele et al.
5,951,475 A 9/1999 Gueziec et al.
5,987,960 A 11/1999 Messner et al.
6,012,216 A 1/2000 Esteves et al.
6,031,888 A 2/2000 Ivan et al.
6,033,415 A 3/2000 Mittelstadt et al.
6,080,181 A 6/2000 Jensen et al.
6,106,511 A 8/2000 Jensen
6,122,541 A 9/2000 Cosman et al.
6,144,875 A 11/2000 Schweikard et al.
6,157,853 A 12/2000 Blume et al.
6,167,145 A 12/2000 Foley et al.
6,167,292 A 12/2000 Badano et al.
6,201,984 B1 3/2001 Funda et al.
6,203,196 B1 3/2001 Meyer et al.
6,205,411 B1 3/2001 DiGioia, III et al.
6,212,419 B1 4/2001 Blume et al.
6,231,565 B1 5/2001 Tovey et al.
6,236,875 B1 5/2001 Bucholz et al.
6,246,900 B1 6/2001 Cosman et al.
6,301,495 B1 10/2001 Gueziec et al.
6,306,126 B1 10/2001 Montezuma
6,312,435 B1 11/2001 Wallace et al.
6,314,311 B1 11/2001 Williams et al.
6,320,929 B1 11/2001 Von Der Haar
6,322,567 B1 11/2001 Mittelstadt et al.
6,325,808 B1 12/2001 Bernard et al.
6,340,363 B1 1/2002 Bolger et al.
6,377,011 B1 4/2002 Ben-Ur
6,379,302 B1 4/2002 Kessman et al.
6,402,762 B2 6/2002 Hunter et al.
6,424,885 B1 7/2002 Niemeyer et al.
6,447,503 B1 9/2002 Wynne et al.
6,451,027 B1 9/2002 Cooper et al.
6,459,926 B1 * 10/2002 Nowlin .................. A61B 34/30
600/102
6,477,400 B1 11/2002 Barrick
6,484,049 B1 11/2002 Seeley et al.
6,487,267 B1 11/2002 Wolter
6,490,467 B1 12/2002 Bucholz et al.
6,490,475 B1 12/2002 Seeley et al.
6,499,488 B1 12/2002 Hunter et al.
6,501,981 B1 12/2002 Schweikard et al.
6,507,751 B2 1/2003 Blume et al.
6,535,756 B1 3/2003 Simon et al.
6,560,354 B1 5/2003 Maurer, Jr. et al.
6,565,554 B1 5/2003 Niemeyer
6,587,750 B2 7/2003 Gerbi et al.
6,614,453 B1 9/2003 Suri et al.
6,614,871 B1 9/2003 Kobiki et al.
6,619,840 B2 9/2003 Rasche et al.
6,636,757 B1 10/2003 Jascob et al.
6,645,196 B1 11/2003 Nixon et al.
6,666,579 B2 12/2003 Jensen
6,669,635 B2 12/2003 Kessman et al.
6,701,173 B2 3/2004 Nowinski et al.
6,757,068 B2 6/2004 Foxlin
6,782,287 B2 8/2004 Grzeszczuk et al.
6,783,524 B2 8/2004 Anderson et al.
6,786,896 B1 9/2004 Madhani et al.
6,788,018 B1 9/2004 Blumenkranz
6,804,581 B2 10/2004 Wang et al.
6,823,207 B1 11/2004 Jensen et al.
6,827,351 B2 12/2004 Graziani et al.
6,837,892 B2 1/2005 Shoham
6,839,612 B2 1/2005 Sanchez et al.
6,856,826 B2 2/2005 Seeley et al.
6,856,827 B2 2/2005 Seeley et al.
6,879,880 B2 4/2005 Nowlin et al.
6,892,090 B2 5/2005 Verard et al.
6,920,347 B2 7/2005 Simon et al.
6,922,632 B2 7/2005 Foxlin
6,968,224 B2 11/2005 Kessman et al.
6,978,166 B2 12/2005 Foley et al.
6,988,009 B2 1/2006 Grimm et al.
6,991,627 B2 1/2006 Madhani et al.
6,996,487 B2 2/2006 Jutras et al.
6,999,852 B2 2/2006 Green
7,007,699 B2 3/2006 Martinelli et al.
7,016,457 B1 3/2006 Senzig et al.
7,043,961 B2 5/2006 Pandey et al.
7,062,006 B1 6/2006 Pelc et al.
7,063,705 B2 6/2006 Young et al.
7,072,707 B2 7/2006 Galloway, Jr. et al.
7,083,615 B2 8/2006 Peterson et al.
7,097,640 B2 8/2006 Wang et al.
7,099,428 B2 8/2006 Clinthorne et al.
7,108,421 B2 9/2006 Gregerson et al.
7,130,676 B2 10/2006 Barrick
7,139,418 B2 11/2006 Abovitz et al.
7,139,601 B2 11/2006 Bucholz et al.
7,155,316 B2 12/2006 Sutherland et al.
7,164,968 B2 1/2007 Treat et al.
7,167,738 B2 1/2007 Schweikard et al.
7,169,141 B2 1/2007 Brock et al.
7,172,627 B2 2/2007 Fiere et al.
7,194,120 B2 3/2007 Wicker et al.
7,197,107 B2 3/2007 Arai et al.
7,231,014 B2 6/2007 Levy
7,231,063 B2 6/2007 Naimark et al.
7,239,940 B2 7/2007 Wang et al.
7,248,914 B2 7/2007 Hastings et al.
7,301,648 B2 11/2007 Foxlin
7,302,288 B1 11/2007 Schellenberg
7,313,430 B2 12/2007 Urquhart et al.
7,318,805 B2 1/2008 Schweikard et al.
7,318,827 B2 1/2008 Leitner et al.
7,319,897 B2 1/2008 Leitner et al.
7,324,623 B2 1/2008 Heuscher et al.
7,327,865 B2 2/2008 Fu et al.
7,331,967 B2 2/2008 Lee et al.
7,333,642 B2 2/2008 Green
7,339,341 B2 3/2008 Oleynikov et al.
7,366,562 B2 4/2008 Dukesherer et al.
7,379,790 B2 5/2008 Toth et al.
7,386,365 B2 6/2008 Nixon
7,422,592 B2 9/2008 Morley et al.
7,435,216 B2 10/2008 Kwon et al.

(56) References Cited

U.S. PATENT DOCUMENTS 7,440,793 B2 10/2008 Chauhan et al.
7,460,637 B2 12/2008 Clinthorne et al.
7,466,303 B2 12/2008 Yi et al.
7,493,153 B2 2/2009 Ahmed et al.
7,505,617 B2 3/2009 Fu et al.
7,533,892 B2 5/2009 Schena et al.
7,542,791 B2 6/2009 Mire et al.
7,555,331 B2 6/2009 Viswanathan
7,567,834 B2 7/2009 Clayton et al.
7,594,912 B2 9/2009 Cooper et al.
7,606,613 B2 10/2009 Simon et al.
7,607,440 B2 10/2009 Coste-Maniere et al.
7,623,902 B2 11/2009 Pacheco
7,630,752 B2 12/2009 Viswanathan
7,630,753 B2 12/2009 Simon et al.
7,643,862 B2 1/2010 Schoenefeld
7,660,623 B2 2/2010 Hunter et al.
7,661,881 B2 2/2010 Gregerson et al.
7,683,331 B2 3/2010 Chang
7,683,332 B2 3/2010 Chang
7,689,320 B2 3/2010 Prisco et al.
7,691,098 B2 4/2010 Wallace et al.
7,702,379 B2 4/2010 Avinash et al.
7,702,477 B2 4/2010 Tuemmler et al.
7,711,083 B2 5/2010 Heigl et al.
7,711,406 B2 5/2010 Kuhn et al.
7,720,523 B2 5/2010 Omernick et al.
7,725,253 B2 5/2010 Foxlin
7,726,171 B2 6/2010 Langlotz et al.
7,742,801 B2 6/2010 Neubauer et al.
7,751,865 B2 7/2010 Jascob et al.
7,760,849 B2 7/2010 Zhang
7,762,825 B2 7/2010 Burbank et al.
7,763,015 B2 7/2010 Cooper et al.
7,787,699 B2 8/2010 Mahesh et al.
7,796,728 B2 9/2010 Bergfjord
7,813,838 B2 10/2010 Sommer
7,818,044 B2 10/2010 Dukesherer et al.
7,819,859 B2 10/2010 Prisco et al.
7,824,401 B2 11/2010 Manzo et al.
7,831,294 B2 11/2010 Viswanathan
7,834,484 B2 11/2010 Sartor
7,835,557 B2 11/2010 Kendrick et al.
7,835,778 B2 11/2010 Foley et al.
7,835,784 B2 11/2010 Mire et al.
7,840,253 B2 11/2010 Tremblay et al.
7,840,256 B2 11/2010 Lakin et al.
7,843,158 B2 11/2010 Prisco
7,844,320 B2 11/2010 Shahidi
7,853,305 B2 12/2010 Simon et al.
7,853,313 B2 12/2010 Thompson
7,865,269 B2 1/2011 Prisco et al.
D631,966 S 2/2011 Perloff et al.
7,879,045 B2 2/2011 Gielen et al.
7,881,767 B2 2/2011 Strommer et al.
7,881,770 B2 2/2011 Melkent et al.
7,886,743 B2 2/2011 Cooper et al.
RE42,194 E 3/2011 Foley et al.
RE42,226 E 3/2011 Foley et al.
7,900,524 B2 3/2011 Calloway et al.
7,907,166 B2 3/2011 Lamprecht et al.
7,909,122 B2 3/2011 Schena et al.
7,925,653 B2 4/2011 Saptharishi
7,930,065 B2 4/2011 Larkin et al.
7,935,130 B2 5/2011 Willliams
7,940,999 B2 5/2011 Liao et al.
7,945,012 B2 5/2011 Ye et al.
7,945,021 B2 5/2011 Shapiro et al.
7,953,470 B2 5/2011 Vetter et al.
7,954,397 B2 6/2011 Choi et al.
7,971,341 B2 7/2011 Dukesherer et al.
7,974,674 B2 7/2011 Hauck et al.
7,974,677 B2 7/2011 Mire et al.
7,974,681 B2 7/2011 Wallace et al.
7,979,157 B2 7/2011 Anvari
7,983,733 B2 7/2011 Viswanathan
7,988,215 B2 8/2011 Seibold
7,996,110 B2 8/2011 Lipow et al.
8,004,121 B2 8/2011 Sartor
8,004,229 B2 8/2011 Nowlin et al.
8,010,177 B2 8/2011 Csavoy et al.
8,019,045 B2 9/2011 Kato
8,021,310 B2 9/2011 Sanborn et al.
8,035,685 B2 10/2011 Jensen
8,046,054 B2 10/2011 Kim et al.
8,046,057 B2 10/2011 Clarke
8,052,688 B2 11/2011 Wolf, II
8,054,184 B2 11/2011 Cline et al.
8,054,752 B2 11/2011 Druke et al.
8,057,397 B2 11/2011 Li et al.
8,057,407 B2 11/2011 Martinelli et al.
8,062,288 B2 11/2011 Cooper et al.
8,062,375 B2 11/2011 Glerum et al.
8,066,524 B2 11/2011 Burbank et al.
8,073,335 B2 12/2011 Labonville et al.
8,079,950 B2 12/2011 Stern et al.
8,086,299 B2 12/2011 Adler et al.
8,092,370 B2 1/2012 Roberts et al.
8,098,914 B2 1/2012 Liao et al.
8,100,950 B2 1/2012 St. Clair et al.
8,105,320 B2 1/2012 Manzo
8,108,025 B2 1/2012 Csavoy et al.
8,109,877 B2 2/2012 Moctezuma de la Barrera et al.
8,112,292 B2 2/2012 Simon
8,116,430 B1 2/2012 Shapiro et al.
8,120,301 B2 2/2012 Goldberg et al.
8,121,249 B2 2/2012 Wang et al.
8,123,675 B2 2/2012 Funda et al.
8,133,229 B1 3/2012 Bonutti
8,142,420 B2 3/2012 Schena
8,147,494 B2 4/2012 Leitner et al.
8,150,494 B2 4/2012 Simon et al.
8,150,497 B2 4/2012 Gielen et al.
8,150,498 B2 4/2012 Gielen et al.
8,165,658 B2 4/2012 Waynik et al.
8,170,313 B2 5/2012 Kendrick et al.
8,179,073 B2 5/2012 Farritor et al.
8,182,476 B2 5/2012 Julian et al.
8,184,880 B2 5/2012 Zhao et al.
8,202,278 B2 6/2012 Orban, III et al.
8,208,708 B2 6/2012 Homan et al.
8,208,988 B2 6/2012 Jensen
8,219,177 B2 7/2012 Smith et al.
8,219,178 B2 7/2012 Smith et al.
8,220,468 B2 7/2012 Cooper et al.
8,224,024 B2 7/2012 Foxlin et al.
8,224,484 B2 7/2012 Swarup et al.
8,225,798 B2 7/2012 Baldwin et al.
8,228,368 B2 7/2012 Zhao et al.
8,231,610 B2 7/2012 Jo et al.
8,239,001 B2 8/2012 Verard et al.
8,241,271 B2 8/2012 Millman et al.
8,248,413 B2 8/2012 Gattani et al.
8,256,319 B2 9/2012 Cooper et al.
8,263,933 B2 9/2012 Zeile
8,271,069 B2 9/2012 Jascob et al.
8,271,130 B2 9/2012 Hourtash
8,281,670 B2 10/2012 Larkin et al.
8,282,653 B2 10/2012 Nelson et al.
8,301,226 B2 10/2012 Csavoy et al.
8,311,611 B2 11/2012 Csavoy et al.
8,320,991 B2 11/2012 Jascob et al.
8,332,012 B2 12/2012 Kienzle, III
8,333,755 B2 12/2012 Cooper et al.
8,335,552 B2 12/2012 Stiles
8,335,557 B2 12/2012 Maschke
8,348,931 B2 1/2013 Cooper et al.
8,353,963 B2 1/2013 Glerum
8,358,818 B2 1/2013 Miga et al.
8,359,730 B2 1/2013 Burg et al.
8,374,673 B2 2/2013 Adcox et al.
8,374,723 B2 2/2013 Zhao et al.
8,379,791 B2 2/2013 Forthmann et al.
8,386,019 B2 2/2013 Camus et al.

(56) References Cited

U.S. PATENT DOCUMENTS 8,392,022 B2 3/2013 Ortmaier et al.
8,394,099 B2 3/2013 Patwardhan
8,395,342 B2 3/2013 Prisco
8,398,634 B2 3/2013 Manzo et al.
8,400,094 B2 3/2013 Schena
8,414,957 B2 4/2013 Enzerink et al.
8,418,073 B2 4/2013 Mohr et al.
8,450,694 B2 5/2013 Baviera et al.
8,452,447 B2 5/2013 Nixon
RE44,305 E 6/2013 Foley et al.
8,462,911 B2 6/2013 Vesel et al.
8,465,476 B2 6/2013 Rogers et al.
8,465,771 B2 6/2013 Wan et al.
8,467,851 B2 6/2013 Mire et al.
8,467,852 B2 6/2013 Csavoy et al.
8,469,947 B2 6/2013 Devengenzo et al.
RE44,392 E 7/2013 Hynes
8,483,434 B2 7/2013 Buehner et al.
8,483,800 B2 7/2013 Jensen et al.
8,486,532 B2 7/2013 Enzerink et al.
8,489,235 B2 7/2013 Moll et al.
8,500,722 B2 8/2013 Cooper
8,500,728 B2 8/2013 Newton et al.
8,504,201 B2 8/2013 Moll et al.
8,506,555 B2 8/2013 Ruiz Morales
8,506,556 B2 8/2013 Schena
8,508,173 B2 8/2013 Goldberg et al.
8,512,318 B2 8/2013 Tovey et al.
8,515,576 B2 8/2013 Lipow et al.
8,518,120 B2 8/2013 Glerum et al.
8,521,331 B2 8/2013 Itkowitz
8,526,688 B2 9/2013 Groszmann et al.
8,526,700 B2 9/2013 Isaacs
8,527,094 B2 9/2013 Kumar et al.
8,528,440 B2 9/2013 Morley et al.
8,532,741 B2 9/2013 Heruth et al.
8,541,970 B2 9/2013 Nowlin et al.
8,548,563 B2 10/2013 Simon et al.
8,549,732 B2 10/2013 Burg et al.
8,551,114 B2 10/2013 Ramos de la Pena
8,551,116 B2 10/2013 Julian et al.
8,556,807 B2 10/2013 Scott et al.
8,556,979 B2 10/2013 Glerum et al.
8,560,118 B2 10/2013 Green et al.
8,561,473 B2 10/2013 Blumenkranz
8,562,594 B2 10/2013 Cooper et al.
8,571,638 B2 10/2013 Shoham
8,571,710 B2 10/2013 Coste-Maniere et al.
8,573,465 B2 11/2013 Shelton, IV
8,574,303 B2 11/2013 Sharkey et al.
8,585,420 B2 11/2013 Burbank et al.
8,594,841 B2 11/2013 Zhao et al.
8,597,198 B2 12/2013 Sanborn et al.
8,600,478 B2 12/2013 Verard et al.
8,603,077 B2 12/2013 Cooper et al.
8,611,985 B2 12/2013 Lavallee et al.
8,613,230 B2 12/2013 Blumenkranz et al.
8,621,939 B2 1/2014 Blumenkranz et al.
8,624,537 B2 1/2014 Nowlin et al.
8,630,389 B2 1/2014 Kato
8,634,897 B2 1/2014 Simon et al.
8,634,957 B2 1/2014 Toth et al.
8,638,056 B2 1/2014 Goldberg et al.
8,638,057 B2 1/2014 Goldberg et al.
8,639,000 B2 1/2014 Zhao et al.
8,641,726 B2 2/2014 Bonutti
8,644,907 B2 2/2014 Hartmann et al.
8,657,809 B2 2/2014 Schoepp
8,660,635 B2 2/2014 Simon et al.
8,666,544 B2 3/2014 Moll et al.
8,675,939 B2 3/2014 Moctezuma de la Barrera
8,678,647 B2 3/2014 Gregerson et al.
8,679,125 B2 3/2014 Smith et al.
8,679,183 B2 3/2014 Glerum et al.
8,682,413 B2 3/2014 Lloyd
8,684,253 B2 4/2014 Giordano et al.
8,685,098 B2 4/2014 Glerum et al.
8,693,730 B2 4/2014 Umasuthan et al.
8,694,075 B2 4/2014 Groszmann et al.
8,696,458 B2 4/2014 Foxlin et al.
8,700,123 B2 4/2014 Okamura et al.
8,706,086 B2 4/2014 Glerum
8,706,185 B2 4/2014 Foley et al.
8,706,301 B2 4/2014 Zhao et al.
8,717,430 B2 5/2014 Simon et al.
8,727,618 B2 5/2014 Maschke et al.
8,734,432 B2 5/2014 Tuma et al.
8,738,115 B2 5/2014 Amberg et al.
8,738,181 B2 5/2014 Greer et al.
8,740,882 B2 6/2014 Jun et al.
8,746,252 B2 6/2014 McGrogan et al.
8,749,189 B2 6/2014 Nowlin et al.
8,749,190 B2 6/2014 Nowlin et al.
8,761,930 B2 6/2014 Nixon
8,764,448 B2 7/2014 Yang et al.
8,771,170 B2 7/2014 Mesallum et al.
8,781,186 B2 7/2014 Clements et al.
8,781,630 B2 7/2014 Banks et al.
8,784,385 B2 7/2014 Boyden et al.
8,786,241 B2 7/2014 Nowlin et al.
8,787,520 B2 7/2014 Baba
8,792,704 B2 7/2014 Isaacs
8,798,231 B2 8/2014 Notohara et al.
8,800,838 B2 8/2014 Shelton, IV
8,808,164 B2 8/2014 Hoffman et al.
8,812,077 B2 8/2014 Dempsey
8,814,793 B2 8/2014 Brabrand
8,816,628 B2 8/2014 Nowlin et al.
8,818,105 B2 8/2014 Myronenko et al.
8,820,605 B2 9/2014 Shelton, IV
8,821,511 B2 9/2014 Von Jako et al.
8,823,308 B2 9/2014 Nowlin et al.
8,827,996 B2 9/2014 Scott et al.
8,828,024 B2 9/2014 Farritor et al.
8,830,224 B2 9/2014 Zhao et al.
8,834,489 B2 9/2014 Cooper et al.
8,834,490 B2 9/2014 Bonutti
8,838,270 B2 9/2014 Druke et al.
8,844,789 B2 9/2014 Shelton, IV et al.
8,855,822 B2 10/2014 Bartol et al.
8,858,598 B2 10/2014 Seifert et al.
8,860,753 B2 10/2014 Bhandarkar et al.
8,864,751 B2 10/2014 Prisco et al.
8,864,798 B2 10/2014 Weiman et al.
8,864,833 B2 10/2014 Glerum et al.
8,867,703 B2 10/2014 Shapiro et al.
8,870,880 B2 10/2014 Himmelberger et al.
8,876,866 B2 11/2014 Zappacosta et al.
8,880,223 B2 11/2014 Raj et al.
8,882,803 B2 11/2014 Iott et al.
8,883,210 B1 11/2014 Truncale et al.
8,888,821 B2 11/2014 Rezach et al.
8,888,853 B2 11/2014 Glerum et al.
8,888,854 B2 11/2014 Glerum et al.
8,894,652 B2 11/2014 Seifert et al.
8,894,688 B2 11/2014 Suh
8,894,691 B2 11/2014 Iott et al.
8,906,069 B2 12/2014 Hansell et al.
8,964,934 B2 2/2015 Ein-Gal
8,992,580 B2 3/2015 Bar et al.
8,996,169 B2 3/2015 Lightcap et al.
9,001,963 B2 4/2015 Sowards-Emmerd et al.
9,002,076 B2 4/2015 Khadem et al.
9,008,757 B2 * 4/2015 Wu ........................ A61B 34/30 600/407
9,044,190 B2 6/2015 Rubner et al.
9,107,683 B2 8/2015 Hourtash et al.
9,119,655 B2 * 9/2015 Bowling ................ A61B 34/10
9,125,556 B2 9/2015 Zehavi et al.
9,131,986 B2 9/2015 Greer et al.
9,215,968 B2 12/2015 Schostek et al.
9,308,050 B2 4/2016 Kostrzewski et al.
9,380,984 B2 7/2016 Li et al.
9,393,039 B2 7/2016 Lechner et al.

(56) References Cited

U.S. PATENT DOCUMENTS 9,398,886 B2 7/2016 Gregerson et al.
9,398,890 B2 7/2016 Dong et al.
9,414,859 B2 8/2016 Ballard et al.
9,420,975 B2 8/2016 Gutfleisch et al.
9,492,235 B2 11/2016 Hourtash et al.
9,592,096 B2 3/2017 Maillet et al.
9,750,465 B2 9/2017 Engel et al.
9,757,203 B2 9/2017 Hourtash et al.
9,795,354 B2 10/2017 Menegaz et al.
9,814,535 B2 11/2017 Bar et al.
9,820,783 B2 11/2017 Donner et al.
9,833,265 B2 12/2017 Donner et al.
9,848,922 B2 12/2017 Tohmeh et al.
9,925,011 B2 3/2018 Gombert et al.
9,931,025 B1 4/2018 Graetzel et al.
10,034,717 B2 7/2018 Miller et al.
2001/0036302 A1 11/2001 Miller
2002/0035321 A1 3/2002 Bucholz et al.
2004/0068172 A1 4/2004 Nowinski et al.
2004/0076259 A1 4/2004 Jensen et al.
2004/0106997 A1 6/2004 Lieberson
2005/0096502 A1 5/2005 Khalili
2005/0143651 A1 6/2005 Verard et al.
2005/0171558 A1 8/2005 Abovitz et al.
2006/0100610 A1 5/2006 Wallace et al.
2006/0173329 A1 8/2006 Marquart et al.
2006/0184396 A1 8/2006 Dennis et al.
2006/0241416 A1 10/2006 Marquart et al.
2006/0291612 A1 12/2006 Nishide et al.
2007/0015987 A1 1/2007 Benlloch Baviera et al.
2007/0021738 A1 1/2007 Hasser et al.
2007/0038059 A1 2/2007 Sheffer et al.
2007/0073133 A1 3/2007 Schoenefeld
2007/0156121 A1 7/2007 Millman et al.
2007/0156157 A1 7/2007 Nahum et al.
2007/0167712 A1 7/2007 Keglovich et al.
2007/0233238 A1 10/2007 Huynh et al.
2008/0004523 A1 1/2008 Jensen
2008/0013809 A1 1/2008 Zhu et al.
2008/0033283 A1 2/2008 Dellaca et al.
2008/0046122 A1 2/2008 Manzo et al.
2008/0082109 A1 4/2008 Moll et al.
2008/0108912 A1 5/2008 Node-Langlois
2008/0108991 A1 5/2008 Von Jako
2008/0109012 A1 5/2008 Falco et al.
2008/0144906 A1 6/2008 Allred et al.
2008/0161680 A1 7/2008 Von Jako et al.
2008/0161682 A1 7/2008 Kendrick et al.
2008/0177203 A1 7/2008 von Jako
2008/0214922 A1 9/2008 Hartmann et al.
2008/0228068 A1 9/2008 Viswanathan et al.
2008/0228196 A1 9/2008 Wang et al.
2008/0235052 A1 9/2008 Node-Langlois et al.
2008/0269596 A1 10/2008 Revie et al.
2008/0287771 A1 11/2008 Anderson
2008/0287781 A1 11/2008 Revie et al.
2008/0300477 A1 12/2008 Lloyd et al.
2008/0300478 A1 12/2008 Zuhars et al.
2008/0302950 A1 12/2008 Park et al.
2008/0306490 A1 12/2008 Lakin et al.
2008/0319311 A1 12/2008 Hamadeh
2009/0012509 A1 1/2009 Csavoy et al.
2009/0030428 A1 1/2009 Omori et al.
2009/0080737 A1 3/2009 Battle et al.
2009/0185655 A1 7/2009 Koken et al.
2009/0198121 A1 8/2009 Hoheisel
2009/0216113 A1 8/2009 Meier et al.
2009/0228019 A1 9/2009 Gross et al.
2009/0259123 A1 10/2009 Navab et al.
2009/0259230 A1 10/2009 Khadem et al.
2009/0264899 A1 10/2009 Appenrodt et al.
2009/0281417 A1 11/2009 Hartmann et al.
2010/0022874 A1 1/2010 Wang et al.
2010/0039506 A1 2/2010 Sarvestani et al.
2010/0125286 A1 5/2010 Wang et al.
2010/0130986 A1 5/2010 Mailloux et al.
2010/0228117 A1 9/2010 Hartmann
2010/0228265 A1 9/2010 Prisco
2010/0249571 A1 9/2010 Jensen et al.
2010/0274120 A1 10/2010 Heuscher
2010/0280363 A1 11/2010 Skarda et al.
2010/0331858 A1 12/2010 Simaan et al.
2011/0022229 A1 1/2011 Jang et al.
2011/0077504 A1 3/2011 Fischer et al.
2011/0098553 A1 4/2011 Robbins et al.
2011/0137152 A1 6/2011 Li
2011/0213384 A1 9/2011 Jeong
2011/0224684 A1 9/2011 Larkin et al.
2011/0224685 A1 9/2011 Larkin et al.
2011/0224686 A1 9/2011 Larkin et al.
2011/0224687 A1 9/2011 Larkin et al.
2011/0224688 A1 9/2011 Larkin et al.
2011/0224689 A1 9/2011 Larkin et al.
2011/0224825 A1 9/2011 Larkin et al.
2011/0230967 A1 9/2011 O'Halloran et al.
2011/0238080 A1 9/2011 Ranjit et al.
2011/0276058 A1 11/2011 Choi et al.
2011/0282189 A1 11/2011 Graumann
2011/0286573 A1 11/2011 Schretter et al.
2011/0295062 A1 12/2011 Solsona et al.
2011/0295370 A1 12/2011 Suh et al.
2011/0306986 A1 12/2011 Lee et al.
2012/0035507 A1 2/2012 George et al.
2012/0046668 A1 2/2012 Gantes
2012/0051498 A1 3/2012 Koishi
2012/0053597 A1 3/2012 Anvari et al.
2012/0059248 A1 3/2012 Holsing et al.
2012/0071753 A1 3/2012 Hunter et al.
2012/0108954 A1 5/2012 Schulhauser et al.
2012/0136372 A1 5/2012 Amat Girbau et al.
2012/0143084 A1 6/2012 Shoham
2012/0184839 A1 7/2012 Woerlein
2012/0197182 A1 8/2012 Millman et al.
2012/0226145 A1 9/2012 Chang et al.
2012/0235909 A1 9/2012 Birkenbach et al.
2012/0245596 A1 9/2012 Meenink
2012/0253332 A1 10/2012 Moll
2012/0253360 A1 10/2012 White et al.
2012/0256092 A1 10/2012 Zingerman
2012/0294498 A1 11/2012 Popovic
2012/0296203 A1 11/2012 Hartmann et al.
2013/0006267 A1 1/2013 Odermatt et al.
2013/0016889 A1 1/2013 Myronenko et al.
2013/0030571 A1 1/2013 Ruiz Morales et al.
2013/0035583 A1 2/2013 Park et al.
2013/0060146 A1 3/2013 Yang et al.
2013/0060337 A1 3/2013 Petersheim et al.
2013/0094742 A1 4/2013 Feilkas
2013/0096574 A1 4/2013 Kang et al.
2013/0113791 A1 5/2013 Isaacs et al.
2013/0116706 A1 5/2013 Lee et al.
2013/0131695 A1 5/2013 Scarfogliero et al.
2013/0144307 A1 6/2013 Jeong et al.
2013/0158542 A1 6/2013 Manzo et al.
2013/0165937 A1 6/2013 Patwardhan
2013/0178867 A1 7/2013 Farritor et al.
2013/0178868 A1 7/2013 Roh
2013/0178870 A1 7/2013 Schena
2013/0204271 A1 8/2013 Brisson et al.
2013/0211419 A1 8/2013 Jensen
2013/0211420 A1 8/2013 Jensen
2013/0218142 A1 8/2013 Tuma et al.
2013/0223702 A1 8/2013 Holsing et al.
2013/0225942 A1 8/2013 Holsing et al.
2013/0225943 A1 8/2013 Holsing et al.
2013/0231556 A1 9/2013 Holsing et al.
2013/0237995 A1 9/2013 Lee et al.
2013/0245375 A1 9/2013 DiMaio et al.
2013/0261640 A1 10/2013 Kim et al.
2013/0272488 A1 10/2013 Bailey et al.
2013/0272489 A1 10/2013 Dickman et al.
2013/0274761 A1 10/2013 Devengenzo et al.
2013/0281821 A1 10/2013 Liu et al.
2013/0296884 A1 11/2013 Taylor et al.

(56) References Cited

U.S. PATENT DOCUMENTS

2013/0303887 A1 11/2013 Holsing et al.
2013/0307955 A1 11/2013 Deitz et al.
2013/0317521 A1 11/2013 Choi et al.
2013/0325033 A1 12/2013 Schena et al.
2013/0325035 A1 12/2013 Hauck et al.
2013/0331686 A1 12/2013 Freysinger et al.
2013/0331858 A1 12/2013 Devengenzo et al.
2013/0331861 A1 12/2013 Yoon
2013/0342578 A1 12/2013 Isaacs
2013/0345717 A1 12/2013 Markvicka et al.
2013/0345757 A1 12/2013 Stad
2014/0001235 A1 1/2014 Shelton, IV
2014/0012131 A1 1/2014 Heruth et al.
2014/0031664 A1 1/2014 Kang et al.
2014/0046128 A1 2/2014 Lee et al.
2014/0046132 A1 2/2014 Hoeg et al.
2014/0046340 A1 2/2014 Wilson et al.
2014/0049629 A1 2/2014 Siewerdsen et al.
2014/0058406 A1 2/2014 Tsekos
2014/0073914 A1 3/2014 Lavallee et al.
2014/0080086 A1 3/2014 Chen
2014/0081128 A1 3/2014 Verard et al.
2014/0088612 A1 3/2014 Bartol et al.
2014/0094694 A1 4/2014 Moctezuma de la Barrera
2014/0094851 A1 4/2014 Gordon
2014/0096369 A1 4/2014 Matsumoto et al.
2014/0100587 A1 4/2014 Farritor et al.
2014/0121676 A1 5/2014 Kostrzewski et al.
2014/0128882 A1 5/2014 Kwak et al.
2014/0130810 A1 5/2014 Azizian et al.
2014/0135796 A1 5/2014 Simon et al.
2014/0142591 A1 5/2014 Alvarez et al.
2014/0142592 A1 5/2014 Moon et al.
2014/0148692 A1 5/2014 Hartmann et al.
2014/0163581 A1 6/2014 Devengenzo et al.
2014/0171781 A1 6/2014 Stiles
2014/0171900 A1 6/2014 Stiles
2014/0171965 A1 6/2014 Loh et al.
2014/0180308 A1 6/2014 von Grunberg
2014/0180309 A1 6/2014 Seeber et al.
2014/0187915 A1 7/2014 Yaroshenko et al.
2014/0188132 A1 7/2014 Kang
2014/0194699 A1 7/2014 Roh et al.
2014/0221819 A1 8/2014 Sarment
2014/0222023 A1 8/2014 Kim et al.
2014/0228631 A1 8/2014 Kwak et al.
2014/0234804 A1 8/2014 Huang et al.
2014/0257328 A1 9/2014 Kim et al.
2014/0257329 A1 9/2014 Jang et al.
2014/0257330 A1 9/2014 Choi et al.
2014/0275760 A1 9/2014 Lee et al.
2014/0275985 A1 9/2014 Walker et al.
2014/0276931 A1 9/2014 Parihar et al.
2014/0276940 A1 9/2014 Seo
2014/0276944 A1 9/2014 Farritor et al.
2014/0288413 A1 9/2014 Hwang et al.
2014/0299648 A1 10/2014 Shelton, IV et al.
2014/0303434 A1 10/2014 Farritor et al.
2014/0303643 A1 10/2014 Ha et al.
2014/0305995 A1 10/2014 Shelton, IV et al.
2014/0309659 A1 10/2014 Roh et al.
2014/0316436 A1 10/2014 Bar et al.
2014/0323803 A1 10/2014 Hoffman et al.
2014/0324070 A1 10/2014 Min et al.
2014/0330288 A1 11/2014 Date et al.
2014/0364720 A1 12/2014 Darrow et al.
2014/0371577 A1 12/2014 Maillet et al.
2015/0039034 A1 2/2015 Frankel et al.
2015/0085970 A1 3/2015 Bouhnik et al.
2015/0146847 A1 5/2015 Liu
2015/0150524 A1 6/2015 Yorkston et al.
2015/0196261 A1 7/2015 Funk
2015/0213633 A1 7/2015 Chang et al.
2015/0335480 A1 11/2015 Alvarez et al.
2015/0342647 A1 12/2015 Frankel et al.
2016/0005194 A1 1/2016 Schretter et al.
2016/0166329 A1 6/2016 Langan et al.
2016/0235480 A1 8/2016 Scholl et al.
2016/0249990 A1 9/2016 Glozman et al.
2016/0302871 A1 10/2016 Gregerson et al.
2016/0320322 A1 11/2016 Suzuki
2016/0331335 A1 11/2016 Gregerson et al.
2017/0135770 A1 5/2017 Scholl et al.
2017/0143284 A1 5/2017 Sehnert et al.
2017/0143426 A1 5/2017 Isaacs et al.
2017/0156816 A1 6/2017 Ibrahim
2017/0202629 A1 7/2017 Maillet et al.
2017/0212723 A1 7/2017 Atarot et al.
2017/0215825 A1 8/2017 Johnson et al.
2017/0215826 A1 8/2017 Johnson et al.
2017/0215827 A1 8/2017 Johnson et al.
2017/0231710 A1 8/2017 Scholl et al.
2017/0258426 A1 9/2017 Risher-Kelly et al.
2017/0273748 A1 9/2017 Hourtash et al.
2017/0296277 A1 10/2017 Hourtash et al.
2017/0360493 A1 12/2017 Zucher et al.

* cited by examiner

SYSTEMS AND METHODS FOR PERFORMING MINIMALLY INVASIVE SPINAL SURGERY WITH A ROBOTIC SURGICAL SYSTEM USING A PERCUTANEOUS TECHNIQUE

CROSS REFERENCE TO RELATED APPLICATIONS

This application is a continuation of U.S. patent application Ser. No. 17/588,992, filed on Jan. 31, 2022 now U.S. 12,076,095), which is a continuation of U.S. patent application Ser. No. 16/720,187, filed on Dec. 19, 2019 now U.S. 11,266,470), which is a continuation of U.S. patent application Ser. No. 15/047,277, filed Feb. 18, 2016 now U.S. Pat. No. 10,555,782), which claims priority to provisional application No. 62/117,919, filed Feb. 18, 2015 (expired), all of which are incorporated in their entirely by reference herein.

BACKGROUND OF THE INVENTION

Robotic-assisted surgical systems have been developed to improve surgical precision and enable the implementation of new surgical procedures. For example, robotic systems have been developed to sense a surgeon's hand movements and translate them to scaled-down micro-movements and filter out unintentional tremors for precise microsurgical techniques in organ transplants, reconstructions, and minimally invasive surgeries. Other robotic systems are directed to telemanipulation of surgical tools such that the surgeon does not have to be present in the operating room, thereby facilitating remote surgery. Feedback-controlled robotic systems have also been developed to provide smoother manipulation of a surgical tool during a procedure than could be achieved by an unaided surgeon.

However, widespread acceptance of robotic systems by surgeons and hospitals is limited for a variety of reasons. Current systems are expensive to own and maintain. They often require extensive preoperative surgical planning prior to use, and they extend the required preparation time in the operating room. They are physically intrusive, possibly obscuring portions of a surgeon's field of view and blocking certain areas around the operating table, such that a surgeon and/or surgical assistants are relegated to one side of the operating table. Current systems may also be non-intuitive or otherwise cumbersome to use, particularly for surgeons who have developed a special skill or "feel" for performing certain maneuvers during surgery and who find that such skill cannot be implemented using the robotic system. Finally, robotic surgical systems may be vulnerable to malfunction or operator error, despite safety interlocks and power backups.

Spinal surgeries often require precision drilling and placement of screws or other implements in relation to the spine, and there may be constrained access to the vertebrae during surgery that makes such maneuvers difficult. Catastrophic damage or death may result from improper drilling or maneuvering of the body during spinal surgery, due to the proximity of the spinal cord and arteries. Common spinal surgical procedures include a discectomy for removal of all or part of a disk, a foraminotomy for widening of the opening where nerve roots leave the spinal column, a laminectomy for removal of the lamina or bone spurs in the back, and spinal fusion for fusing of two vertebrae or vertebral segments together to eliminate pain caused by movement of the vertebrae.

Spinal surgeries that involve screw placement require preparation of holes in bone (e.g., vertebral segments) prior to placement of the screws. Where such procedures are performed manually, in some implementations, a surgeon judges a drill trajectory for subsequent screw placement on the basis of pre-operative CT scans. Other manual methods which do not involve usage of the pre-operative CT scans, such as fluoroscopy, 3D fluoroscopy or natural landmark-based, may be used to determine the trajectory for preparing holes in bone prior to placement of the screws. In some implementations, the surgeon holds the drill in his hand while drilling, and fluoroscopic images are obtained to verify if the trajectory is correct. Some surgical techniques involve usage of different tools, such as a pedicle finder or K-wires. Such procedures rely strongly on the expertise of the surgeon, and there is significant variation in success rate among different surgeons. Screw misplacement is a common problem in such surgical procedures.

Image-guided spinal surgeries involve optical tracking to aid in screw placement. However, such procedures are currently performed manually, and surgical tools can be inaccurately positioned despite virtual tracking. A surgeon is required to coordinate his real-world, manual manipulation of surgical tools using images displayed on a two dimensional screen. Such procedures can be non-intuitive and require training, since the surgeon's eye must constantly scan both the surgical site and the screen to confirm alignment. Furthermore, procedural error can result in registration inaccuracy of the image-guiding system, rendering it useless, or even misleading.

Certain force feedback systems are used by surgeons in certain procedures; however such systems have a large footprint and take up valuable, limited space in the operating room. These systems also require the use of surgical tools that are specially adapted for use with the force feedback system, and the training required by surgeons to operate such systems can be significant. Moreover, surgeons may not be able to use expertise they have developed in performing spinal surgeries when adapting to use of the current force feedback systems. Such systems, while precise, may require more surgical time and more operating room preparation time to ready placement of the equipment for surgery.

Traditional open surgery techniques for spinal surgeries are very invasive for the patient. They require relatively big openings which increases the risk of infections, tissue destruction and recovery time. Scar may be large and reduce patient's confort and appreciation of the procedure. Thus, there is a need for systems, apparatus, and methods that provide enhanced precision in performing surgeries such as spinal surgeries.

SUMMARY OF THE INVENTION

Described herein are systems, apparatus, and methods for precise placement and guidance of tools during surgery, particularly spinal surgery, using minimally invasive surgical techniques. Several minimally invasive approaches to spinal surgeries were conceived, percutaneous technique being one of them. This procedures looks to establish a skin opening as small as possible by accessing inner organs via needle-puncture of the skin. The percutaneous technique is used in conjunction with a robotic surgical system to further enhance advantages of manual percutaneous techniques by improving precision, usability and/or shortening surgery time by removal of redundant steps.

The system, in certain embodiments, features a portable robot arm with end effector for precise positioning of a surgical tool. Minimally invasive surgical techniques are used to obtain access to vertebrae while protecting soft tissues in the surrounding area. These techniques minimize blood loss, postoperative pain, and scaring while providing for faster recoveries.

The disclosed technology, in certain embodiments, includes a method of performing minimally invasive spinal surgery with a robotic surgical system using a percutaneous technique. The method includes, in certain embodiments, detecting, by a force sensor (e.g., on a robotic arm; e.g., between a robotic arm and an end effector), movement (e.g., by a surgeon) of a surgical instrument guide attached to a robotic arm of the robotic surgical system. The surgical instrument guide, in certain embodiments, defines a trajectory comprising a location and an orientation (e.g., a 3-dimensional vector) for insertion of a medical implant (e.g., screw) in a vertebra of a patient.

The method may include storing, by a processor of a computer device, a planned trajectory based on the trajectory of the surgical instrument guide at a defined time (e.g., upon receiving instruction to store the trajectory as the planned trajectory; e.g., when the surgeon is satisfied with the trajectory) (e.g., wherein the planned trajectory defines the place for an incision). In certain embodiments, after the planned trajectory is defined, the method includes detecting, by the force sensor, movement of the surgical instrument guide towards the vertebra.

In certain embodiments, the method includes constraining and/or maintaining, by the processor, an orientation of the surgical instrument guide along the planned trajectory as the surgical instrument guide is moved (e.g., by a surgeon; e.g., by a surgeon physically touching a portion of the robotic arm and/or end effector) through an incision to (e.g., adjacent or near) a surface of the vertebra.

In certain embodiments, the method includes maintaining, by the processor, a position of the surgical instrument guide as a surgeon passes a drill through the surgical instrument guide and drills a hole in the vertebra. In certain embodiments, the method includes constraining and/or maintaining, by the processor, an orientation of the surgical instrument guide along the planned trajectory as the surgical instrument guide is moved (e.g., by a surgeon; e.g., by a surgeon physically touching a portion of the robotic arm and/or end effector) away from the vertebra (e.g., such that a medical implant (e.g., screw) can be inserted into the hole in the vertebra).

In certain embodiments, the method includes maintaining, by the processor, a position of the surgical instrument guide as a k-wire (e.g., flexible k-wire) is inserted into the hole in the vertebrae (e.g., along the planned trajectory such that the orientation of the k-wire substantially represents the planned trajectory) (e.g., thereby saving the trajectory for future retrieval (e.g., after the surgical instrument guide is removed).

In certain embodiments, the disclosed technology includes an adaptive tube sized and shaped to fit in the surgical instrument guide and receive a k-wire therethrough (e.g., to guide the k-wire into the hole in the vertebra).

In certain embodiments, the method includes providing, by the processor, for display on a graphical user interface, a composite image comprising a visual representation of the trajectory superimposed with a medical image of the vertebra of the patient;

In certain embodiments, the method includes, after the surgical instrument guide is moved through the incision, detecting, by a force sensor, movement of the surgical instrument guide (e.g., as a surgeon adjusts (e.g., fine adjustment) the planned trajectory); and storing, by the processor, an updated planned trajectory (e.g., as the planned trajectory).

In certain embodiments, the surgeon decouples a translation movement of the surgical instrument guide from a rotation movement of the surgical instrument guide.

In certain embodiments, the method includes maintaining a position of the surgical instrument guide as a surgeon passes a tap through the surgical instrument guide and taps the hole in the vertebra. In certain embodiments, the method includes tapping, by a surgeon, the hole in the vertebra (e.g., by sliding a tap along the k-wire to orient the k-wire relative to the hole).

In certain embodiments, the method includes placing, by the surgeon, the screw in the hole in the vertebra (e.g., wherein the hole is tapped or untapped) (e.g., using a screw driver that is slide along the k-wire; e.g., using a navigation system to guide the surgeon (e.g., without a k-wire)). In certain embodiments, the method includes the medical implant is a screw. In certain embodiments, the method includes the medical implant is a screw, and an extensor is attached to the back of the screw.

In certain embodiments, the method includes inserting, by a surgeon, along the trajectory, a medical implant (e.g., a screw) into the hole in the vertebra. In certain embodiments, the method includes, before the surgical instrument guide is moved through the incision, cutting, by a surgeon, at least one of the patient's muscles and skin, thereby creating a working channel.

In certain embodiments, the method includes maneuvering a first dilator to access a vertebrae of a patient through the patient's muscles and skin, wherein the dilator defines a working channel for accessing the vertebrae; and increasing the size of the working channel (e.g., using one or more dilators subsequent to the first dilator, whereby a subsequent dilator is temporarily secured in the patient tissue).

In certain embodiments, the method includes removing one or more dilators prior to inserting the medical implant (e.g., screw).

During minimally invasive surgical procedures, dilators may be used to create a working channel through which an operation is performed. The dilators may be a set of tubes with increasing diameters which are inserted into a small incision one at a time until the desired diameter of the working channel is achieved. The dilators may be used with a robotic surgical system (e.g., attached to the robotic arm) to perform a minimally invasive surgery. This allows the usage, in certain embodiments, of standard dilators and a robotic surgical system to provide precise guidance of surgical tools through a dilator and greater flexibility. The dilator may be held by the robot and automatically repositioned when the surgeon adjusts the trajectory along which, for example, a hole is prepared in a vertebra. Adjustment of the end effector of the robotic surgical system automatically adjusts an angle and/or position of the dilator attached to the robot with respect to the vertebrae and aligns an axis defined by the dilator with a desired trajectory during a surgical procedure without removal of the dilator from the patient tissue during the repositioning.

For example, first dilator may be used to access a vertebrae of a patient through the patient's muscles and skin, thereby defining a working channel for accessing the vertebrae. One or more subsequent dilators may be slid over the first dilator. Each of the one or more subsequent dilators are configured to be positioned over the preceding dilators and increase the size of the working channel. Each dilator except the last added dilator is configured to be removed from the patient thereby leaving the last added dilator. The last added dilator is configured to be attached to an end effector of a robotic arm using a dilator fixator. A manipulator is configured to allow robotically-assisted or unassisted positioning and/or movement of the last added dilator by a user with at least four degrees of freedom to align an axis defined by the last added dilator with respect to the vertebrae. Adjustment of the manipulator automatically adjusts an angle and/or position of the attached dilator with respect to the vertebrae and aligns an axis defined by the attached dilator with a desired trajectory during a surgical procedure without removal of the attached dilator from the patient tissue during the repositioning.

The system requires only minimal training by surgeons/operators, is intuitive to use, and has a small footprint with significantly reduced obstruction of the operating table. The system works with existing, standard surgical tools, does not require increased surgical time or preparatory time, and safely provides the enhanced precision achievable by robotic-assisted systems. Moreover, the system allows for a desired trajectory (e.g., for a drill guide during spinal surgery) to be set in a variety of manners based on the circumstances of the surgery. For example, some surgical procedures are planned pre-operatively with the surgeon defining the desired position of an implant using imaging technology, such as CT images (e.g., 3D CT images). The desired position of the implant may also be determined and proposed by the system. In the operating room the surgeon may be guided by the robotic system (e.g., robotic guidance of the surgical tools) to accurately execute the planning.

A mobile cart houses a robot arm with an end effector that holds various standard surgical tools/implants, such as a drill or screw. Positioning such surgical tools with precision is critical. The robot arm provides more precise, stable placement of such tools than can be achieved manually, where placement is guided, yet intuitive. The mobile cart permits easy set-up and use of the system. Once stabilization is engaged, the mobile cart is secured in place on the operating room floor and cannot move. In certain embodiments, the robot cart houses the robot, robot controller, supervisor interlock system, power system, riding system, and interface to the navigation system.

The disclosed technology, in certain embodiments, includes a method of performing minimally invasive spinal surgery with a robotic surgical system. The method may include: maneuvering a first dilator (defining a working channel for accessing the vertebrae) to access a vertebrae of a patient through the patient's muscles and skin; increasing the size of the working channel (e.g., using one or more dilators subsequent to the first dilator, whereby a subsequent dilator is temporarily secured in the patient tissue); attaching the first dilator or a subsequent dilator to the end effector of the robotic arm using a dilator fixator; and following attachment of the first or a subsequent dilator to the end effector, repositioning the end effector thereby automatically adjusting an angle and/or position of the attached dilator with respect to the vertebrae and aligning an axis defined by the attached dilator with a desired trajectory during a surgical procedure without removal of the attached dilator from the patient tissue during the repositioning.

Increasing the size of the working channel may include maneuvering a second dilator over the first dilator, wherein the second dilator is sized and shaped to slide over the first dilator and increase the size of the working channel; and, after positioning the second dilator over the first dilator (and/or after positioning one or more subsequent dilators over the preceding dilators), removing the first dilator (and/or other previous dilators except the final added dilator) from the patient, thereby leaving the last added dilator, wherein the attached dilator is the last added dilator. In certain embodiments, the attached dilator is the dilator with largest circumference.

In certain embodiment, increasing the size of the working channel includes expanding the diameter of the first dilator thereby increasing the diameter of the working channel, wherein the dilator attached to the end effector is the first dilator.

The method, in certain embodiments, includes placing a surgical instrument guide inside of the attached dilator, wherein the surgical instrument guide is sized and shaped to fit at least partially inside the attached dilator along an axis defined by said dilator. The end effector may include a surgical instrument guide attached thereto, configured to hold and/or restrict movement of a surgical instrument therethrough. The surgical instrument guide may include at least one of a drill bit guide, tap guide, screwdriver guide, screw guide, awl guide, and implant guide. The surgical instrument may be at least one of a drill bit, tap, screwdriver, screw, implant, and awl, wherein the surgical instrument is configured to slide through the surgical instrument guide. The attached dilator may be configured to hold and/or restrict movement of a surgical instrument therethrough.

The method, in certain embodiments, includes registering the patient, wherein registering the patient comprises identifying the transformation between the actual patient anatomy and one or more medical images; maneuvering the end effector towards the vertebrae on which the surgeon will operate; determining, by a processor of a computing device, an ideal implant trajectory; and providing, by the processor, for display on a graphical user interface, the ideal implant trajectory for review by the surgeon, wherein (i) the surgeon may adapt the ideal implant trajectory if needed using hands-on planning, and (ii) the surgeon acknowledges the ideal implant trajectory or the adapted trajectory thereby causing the acknowledged trajectory to be stored as the desired trajectory.

The method may include, prior to maneuvering the attached dilator: moving a mobile cart transporting a robotic surgical system comprising a robotic arm in proximity to an operating table, wherein the robotic arm has an end effector; and stabilizing the mobile cart.

The disclosed technology, in certain embodiments, includes a robotic surgical system for performing minimally invasive surgery. The system may include: a robotic arm with an end effector; a first dilator to access a vertebrae of a patient through the patient's muscles and skin, wherein the first dilator defines a working channel for accessing the vertebrae; one or more subsequent dilators sized and shaped to slide over the first dilator and/or one or more of the one or more subsequent dilators. The one or more subsequent dilators may include a last added dilator, and each of the one or more subsequent dilators are configured to be positioned over the preceding dilators and increase the size of the working channel. Each dilator except the last added dilator may be configured to be removed from the patient thereby leaving the last added dilator, and the last added dilator may be configured to be attached to the end effector of the robotic arm using a dilator fixator.

The system may include a manipulator configured to allow robotically-assisted or unassisted positioning and/or movement of the end effector by a user with at least four degrees of freedom thereby automatically adjusting an angle and/or position of the last added dilator with respect to the vertebrae and aligning an axis defined by the last added dilator with a desired trajectory during a surgical procedure without removal of the last added dilator from the patient tissue during the repositioning.

Each one or more subsequent dilators may have a circumference larger than the circumference of the first dilator, and the one or more subsequent dilators increase the size of the working channel as each subsequent dilator is added.

The system may include a surgical instrument guide configured to be placed inside of the attached dilator, wherein the surgical instrument guide is sized and shaped to fit at least partially inside the attached dilator along an axis defined by the dilator. The end effector may include the surgical instrument guide attached thereto, configured to hold and/or restrict movement of a surgical instrument therethrough. The surgical instrument guide is may be a drill bit guide, tap guide, screwdriver guide, screw guide, awl guide, and implant guide. The surgical instrument may be a drill bit, tap, screwdriver, screw, implant, and awl, wherein the surgical instrument is configured to slide through the surgical instrument guide.

The attached dilator may be the dilator with largest circumference. The attached dilator may be configured to hold and/or restrict movement of a surgical instrument therethrough.

In certain embodiments, the system includes: a processor; and a memory, the memory storing instructions that, when executed by the processor, cause the processor to: store a transformation between the actual patient anatomy and one or more medical images; determine an ideal implant trajectory; and provide, for display on a graphical user interface, the ideal implant trajectory for review by the surgeon, wherein (i) the surgeon may adapt the ideal implant trajectory if needed using hands-on planning, and (ii) the surgeon acknowledges the ideal implant trajectory or the adapted trajectory thereby causing the acknowledged trajectory to be stored as the desired trajectory.

The disclosed technology, in certain embodiments, may include a robotic surgical system for performing minimally invasive surgery with a robotic arm with an end effector; a dilator to access a vertebrae of a patient through the patient's muscles and skin; and a manipulator configured to allow robotically-assisted or unassisted positioning and/or movement of the end effector by a user with at least four degrees of freedom thereby automatically adjusting an angle and/or position of the dilator with respect to the vertebrae and aligning an axis defined by the dilator with a desired trajectory during a surgical procedure without removal of the dilator from the patient tissue during the repositioning. The dilator may define a working channel for accessing the vertebrae. The dilator may be configured to be expanded to increase the size of the working channel and be attached to an end effector of a robotic arm using a dilator fixator.

The system may include a surgical instrument guide configured to be placed inside of the dilator. The surgical instrument guide is sized and shaped to fit at least partially inside the dilator along an axis defined by the dilator. The end effector may include the surgical instrument guide attached thereto, configured to hold and/or restrict movement of a surgical instrument therethrough.

The robotic arm may be configured to be maneuvered to a desired position to align an axis defined by the surgical instrument guide at a desired trajectory in relation to the vertebrae. The dilator connected to the end effector of the robotic arm may be automatically positioned as the robotic arm is maneuvered to adjust to the desired trajectory. The dilator is configured to hold and/or restrict movement of a surgical instrument therethrough.

The system may include a processor; and a memory, the memory storing instructions that, when executed by the processor, cause the processor to: store a transformation between the actual patient anatomy and one or more medical images; determine an ideal implant trajectory; and provide, for display on a graphical user interface, the ideal implant trajectory for review by the surgeon, wherein (i) the surgeon may adapt the ideal implant trajectory if needed using hands-on planning, and (ii) the surgeon acknowledges the ideal implant trajectory or the adapted trajectory thereby causing the acknowledged trajectory to be stored as the desired trajectory.

In one aspect, the disclosed technology includes a robotic surgical system including a processor programmed to: detect, via a force sensor (e.g., on a robotic arm; e.g., between a robotic arm and an end effector), movement (e.g., by a surgeon) of a surgical instrument guide attached to a robotic arm of the robotic surgical system, wherein the surgical instrument guide defines a trajectory comprising a location and an orientation (e.g., a 3-dimensional vector) for insertion of a medical implant (e.g., screw) in a vertebra of a patient; store, a planned trajectory based on the trajectory of the surgical instrument guide at a defined time (e.g., upon receiving instruction to store the trajectory as the planned trajectory; e.g., when the surgeon is satisfied with the trajectory) (e.g., wherein the planned trajectory defines the place for an incision); after the planned trajectory is defined, detect, via the force sensor, movement of the surgical instrument guide towards the vertebra; constrain and/or maintain an orientation of the surgical instrument guide along the planned trajectory as the surgical instrument guide is moved (e.g., by a surgeon; e.g., by a surgeon physically touching a portion of the robotic arm and/or end effector) through an incision to (e.g., adjacent or near) a surface of the vertebra; maintain a position of the surgical instrument guide as a surgeon passes a drill through the surgical instrument guide and drills a hole in the vertebra; and constrain and/or maintain an orientation of the surgical instrument guide along the planned trajectory as the surgical instrument guide is moved (e.g., by a surgeon; e.g., by a surgeon physically touching a portion of the robotic arm and/or end effector) away from the vertebra (e.g., such that a medical implant (e.g., screw) can be inserted into the hole in the vertebra).

In certain embodiments, the processor is programmed to: maintain a position of the surgical instrument guide as a k-wire (e.g., flexible k-wire) is inserted into the hole in the vertebrae (e.g., along the planned trajectory such that the orientation of the k-wire substantially represents the planned trajectory) (e.g., thereby saving the trajectory for future retrieval (e.g., after the surgical instrument guide is removed).

In certain embodiments, the system includes an adaptive tube sized and shaped to fit in the surgical instrument guide and receive a k-wire therethrough (e.g., to guide the k-wire into the hole in the vertebra).

In certain embodiments, the system includes a graphical user interface for display of a composite image comprising a visual representation of the trajectory superimposed with a medical image of the vertebra of the patient.

In certain embodiments, the processor is programmed to: after the surgical instrument guide is moved through the incision, detect, via a force sensor, movement of the surgical instrument guide (e.g., as a surgeon adjusts (e.g., fine adjustment) the planned trajectory); and store an updated planned trajectory (e.g., as the planned trajectory).

In certain embodiments, the processor is programmed to permit a translation movement of the surgical instrument guide (e.g., by a surgeon) decoupled from a rotation movement of the surgical instrument guide.

In certain embodiments, the processor is programmed to: maintain a position of the surgical instrument guide as a surgeon passes a tap through the surgical instrument guide and taps the hole in the vertebra.

In certain embodiments, the system includes one or more members selected from the group consisting of the robotic arm, the force sensor, the end effector, and the surgical instrument guide.

In certain embodiments, the incision is from 1 mm to 25 mm, 5 mm to 20 mm, or 10 mm to 15 mm.

In another aspect, the disclosed technology includes a method of operating a robotic surgical system, the method including: detecting, by a force sensor (e.g., on a robotic arm; e.g., between a robotic arm and an end effector), movement (e.g., by a surgeon) of a surgical instrument guide attached to a robotic arm of the robotic surgical system, wherein the surgical instrument guide defines a trajectory comprising a location and an orientation (e.g., a 3-dimensional vector) for insertion of a medical implant (e.g., screw) in a vertebra of a patient; storing, by a processor of a computer device, a planned trajectory based on the trajectory of the surgical instrument guide at a defined time (e.g., upon receiving instruction to store the trajectory as the planned trajectory; e.g., when the surgeon is satisfied with the trajectory) (e.g., wherein the planned trajectory defines the place for an incision); after the planned trajectory is defined, detecting, by the force sensor, movement of the surgical instrument guide towards the vertebra; constraining and/or maintaining, by the processor, an orientation of the surgical instrument guide along the planned trajectory as the surgical instrument guide is moved (e.g., by a surgeon; e.g., by a surgeon physically touching a portion of the robotic arm and/or end effector) through an incision to (e.g., adjacent or near) a surface of the vertebra; maintaining, by the processor, a position of the surgical instrument guide as a surgeon passes a drill through the surgical instrument guide and drills a hole in the vertebra; and constraining and/or maintaining, by the processor, an orientation of the surgical instrument guide along the planned trajectory as the surgical instrument guide is moved (e.g., by a surgeon; e.g., by a surgeon physically touching a portion of the robotic arm and/or end effector) away from the vertebra (e.g., such that a medical implant (e.g., screw) can be inserted into the hole in the vertebra).

In certain embodiments, the method includes maintaining, by the processor, a position of the surgical instrument guide as a k-wire (e.g., flexible k-wire) is inserted into the hole in the vertebrae (e.g., along the planned trajectory such that the orientation of the k-wire substantially represents the planned trajectory) (e.g., thereby saving the trajectory for future retrieval (e.g., after the surgical instrument guide is removed).

In certain embodiments, the system includes an adaptive tube sized and shaped to fit in the surgical instrument guide and receive a k-wire therethrough (e.g., to guide the k-wire into the hole in the vertebra).

In certain embodiments, the method includes providing, by the processor, for display on a graphical user interface, a composite image comprising a visual representation of the trajectory superimposed with a medical image of the vertebra of the patient.

In certain embodiments, the method includes, after the surgical instrument guide is moved through the incision, detecting, by a force sensor, movement of the surgical instrument guide (e.g., as a surgeon adjusts (e.g., fine adjustment) the planned trajectory); and storing, by the processor, an updated planned trajectory (e.g., as the planned trajectory).

In certain embodiments, the surgeon decouples a translation movement of the surgical instrument guide from a rotation movement of the surgical instrument guide.

In certain embodiments, the method includes maintaining a position of the surgical instrument guide as a surgeon passes a tap through the surgical instrument guide and taps the hole in the vertebra.

In certain embodiments, the method includes tapping, by a surgeon, the hole in the vertebra (e.g., by sliding a tap along the k-wire to orient the k-wire relative to the hole).

In certain embodiments, the method includes placing, by the surgeon, the screw in the hole in the vertebra (e.g., wherein the hole is tapped or untapped) (e.g., using a screw driver that is slid along the k-wire; e.g., using a navigation system to guide the surgeon (e.g., without a k-wire)).

In certain embodiments, the medical implant comprises a screw.

In certain embodiments, the medical implant comprises a screw, and an extensor is attached to the back of the screw.

In certain embodiments, the method includes inserting, by a surgeon, along the trajectory, a medical implant (e.g., a screw) into the hole in the vertebra.

In certain embodiments, the method includes, before the surgical instrument guide is moved through the incision, cutting, by a surgeon, at least one of the patient's muscles and skin, thereby creating a working channel.

In certain embodiments, the method includes maneuvering a first dilator to access a vertebra of a patient through the patient's muscles and skin, wherein the dilator defines a working channel for accessing the vertebra; and increasing the size of the working channel (e.g., using one or more dilators subsequent to the first dilator, whereby a subsequent dilator is temporarily secured in the patient tissue).

In certain embodiments, the method includes removing one or more dilators prior to inserting the medical implant (e.g., screw).

In certain embodiments, the incision is from 1 mm to 25 mm, 5 mm to 20 mm, or 10 mm to 15 mm.

BRIEF DESCRIPTION OF THE FIGURES

The foregoing and other objects, aspects, features, and advantages of the present disclosure will become more apparent and better understood by referring to the following description taken in conjunction with the accompanying drawings, in which.

Figure 1:
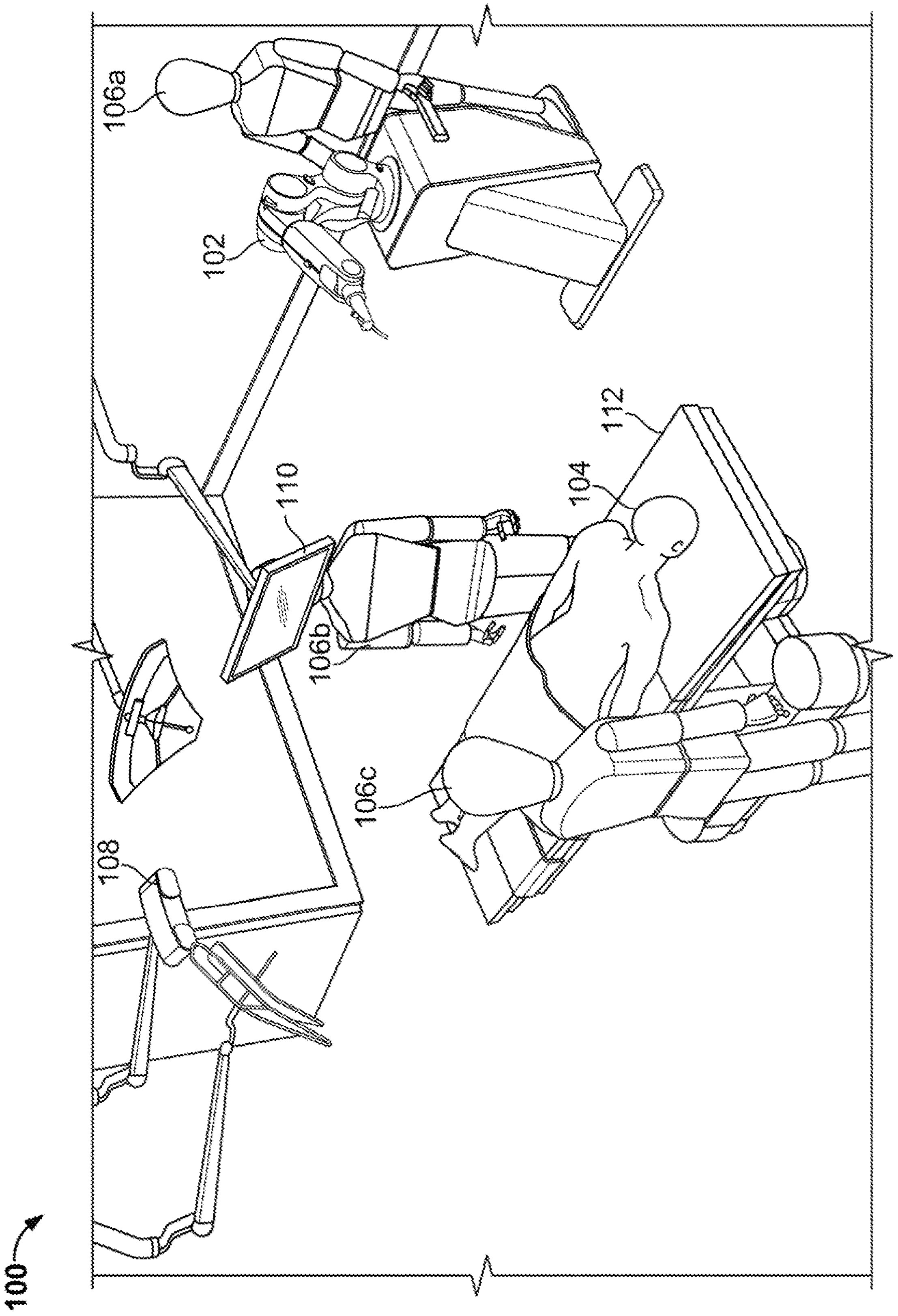
FIG. 1 is a diagram of an operating room in which a mobile cart housing a robotic system for a robotic-assisted spinal surgical procedure is positioned, in accordance with various embodiments of the disclosed technology.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION OF THE INVENTION

FIG. 1 illustrates an example surgical robotic system in an operating room 100. In some implementations, one or more surgeons, surgical assistants, surgical technologists and/or other technicians, (106*a-c*) perform an operation on a patient 104 using a robotic-assisted surgical system. In certain embodiments, the operation may comprise insertion of one or more medical implants (e.g., screws) into the spine of a patient. The robotic system comprises an end effector which can be used to precisely define a trajectory (e.g., intraoperatively. For example, a surgeon may grab the end effector (e.g., a surgical instrument tube or a handle) and move the end effector such a desired trajectory is defined by the end effector (e.g., surgical instrument). Specifically, in the context of a surgical instrument guide, the surgeon may move the guide such that the trajectory along the length of the guide (e.g., the center of the guide) is in the desired position.

The trajectory can be displayed on a computer screen, thereby providing a surgeon with the ability to precisely orient the trajectory. The robotic surgical system assists the surgeon in precisely perform various steps in the surgery, such as drilling, tapping, dilating, and insertion of the screw (e.g., by maintaining the position of a surgical instrument guide relative to a vertebra—in some implementations, the guide moves to track movement of the vertebra).

Moreover, when desired (e.g., once the desired trajectory has been identified), the robot is prevented from moving in any direction but along the trajectory. As a surgeon maneuvers the surgical instrument guide, the control unit of the robotic surgical system restricts the movement of the surgical instrument guide to the defined trajectory. The surgeon can maneuver the surgical instrument guide closely to the patient's skin and pause the movement. The surgeon then cuts the muscle and skin tissue of the patient. The surgeon may entire a fine tuning mode such that very fine, precise adjustments can be made as the surgical instrument guide approaches the vertebra or when the guide is at/near the vertebra. Thus the surgeon can progress the surgical instrument guide through the muscle and skin of the patient along the new trajectory, thereby increasing the precision of the insertion.

One or more dilators may be used with the robotic surgical system to perform a minimally invasive surgery. The dilators may be used to provide a working channel through which the operation is performed. Standard dilators may be used with a robotic surgical system to provide precise guidance of surgical tools. A dilator may be held by the robot and automatically repositioned when the surgeon adjusts the trajectory for performing the surgery. The dilator itself may be used as a surgical instrument guide along with dilator adaptors that adjust the diameter of a portion of the dilator to allow for different sized tools to be guided by the dilator. Surgical instrument guides may also be held by the robotic arm such that tools are guided by a surgical instrument guide through the dilator to perform a medical procedure. Throughout this specification, the terms surgical instrument guide and dilator may be used interchangeably when related to the function of guiding or constraining the robotic-assisted surgical system or a surgical instrument.

For example, first dilator may be used to access a vertebrae of a patient through the patient's muscles and skin. Subsequent dilators are configured to be positioned over the preceding dilators and increase the size of the working channel. Each dilator except the last added dilator is configured to be removed from the patient thereby leaving the last added dilator. The last added dilator is configured to be attached to an end effector of a robotic arm using a dilator fixator. In another example, the dilator inserted into the patient may be designed to expand thereby increasing the diameter of the working channel without adding additional dilators.

A manipulator is configured to allow robotically-assisted or unassisted positioning and/or movement of the surgical instrument guide by a user with at least four degrees of freedom to align an axis defined by the surgical instrument guide with respect to the vertebrae. Adjustment of the manipulator automatically adjusts an angle and/or position of the attached surgical instrument guide with respect to the vertebrae and aligns an axis defined by the attached surgical instrument guide with a desired trajectory during a surgical procedure without removal of the attached surgical instrument guide from the patient tissue during the repositioning.

In some implementations, the surgical robotic system includes a surgical robot 102 on a mobile cart. The surgical robot 102 may be positioned in proximity to an operating table 112 without being attached to the operating table, thereby providing maximum operating area and mobility to surgeons around the operating table and reducing clutter on the operating table. In alternative embodiments, the surgical robot (or cart) is securable to the operating table. In certain embodiments, both the operating table and the cart are secured to a common base to prevent any movement of the cart or table in relation to each other, even in the event of an earth tremor.

In some implementations, the footprint of the mobile cart is small (for example, no greater than 682 millimeters by 770 millimeters), thereby permitting improved access by a surgeon of both sides of an operating table at which the mobile cart is positioned during an operation.

The mobile cart may permit a user (operator) 106*a*, such as a technician, nurse, surgeon, or any other medical personnel in the operating room, to move the surgical robot 102 to different locations before, during, and/or after a surgical procedure. The mobile cart enables the surgical robot 102 to be easily transported into and out of the operating room 100. For example, a user 106*a* may move the surgical robot into the operating room from a storage location. In some implementations, the mobile cart may include wheels, a track system, such as a continuous track propulsion system, or other similar mobility systems for translocation of the cart. The mobile cart may include an attached or embedded handle for locomotion of the mobile cart by an operator.

In some implementations, the wheels include a locking mechanism that prevents the cart from moving. The stabilizing, braking, and/or locking mechanism may be activated when the machine is turned on. In some implementations, the mobile cart includes multiple stabilizing, braking, and/or locking mechanisms. In some implementations, the stabilizing mechanism is electro-mechanical with electronic activation. The stabilizing, braking, and/or locking mechanism(s) may be entirely mechanical. The stabilizing, braking, and/or locking mechanism(s) may be electronically activated and deactivated.

In some implementations, the surgical robot 102 includes a robotic arm mounted on a mobile cart. An actuator may move the robotic arm. The robotic arm may include a force control end-effector configured to hold a surgical tool. The robot may be configured to control and/or allow positioning and/or movement of the end-effector with at least four degrees of freedom (e.g., six degrees of freedom, three translations and three rotations).

In some implementations, the robotic arm is configured to releasably hold a surgical tool, allowing the surgical tool to be removed and replaced with a second surgical tool. The system may allow the surgical tools to be swapped without re-registration, or with automatic or semi-automatic re-registration of the position of the end-effector. Registration spatially aligns the robot, patient (e.g., spine) and the desired trajectory. A marker may be coupled or associated with a vertebrae or other bone to assist with the registration process. The location of the marker is determined by the system. The system stores this position. The position of the vertebrae is thus known. The position of other bones may also be determined with reference to the marker. Once the registration is complete, tracking and/or immobilization ensure that the registration (e.g., spatial orientation) is maintained. Immobilization typically fixes the patient or bone (e.g., spine) with respect to the robot. In contrast, tracking system tracks the position of the patient or the bone (e.g., by tracking the movement of the marker or position of the marker relative to the robot) as described in relation to FIGS. 1 and 3.

In some implementations, the surgical robot 102 includes a robotic arm comprising joints allowing the arm to be automatically positioned upon user command into various different predetermined configurations convenient for various preparatory, readying, and storage procedures. For example, the surgical robot 102 may be arranged in a standby configuration. In a standby configuration, the robotic arm of surgical robot 102 may be arranged in a compacted standby configuration that, for example, facilitates easy and compact storage of surgical robot 102 when it is not in use. Other configurations may include a drape configuration in which the robot arm is extended to facilitate placement of a sterile surgical drape over the robot and cart, and a preparation configuration in which the robot arm is positioned prior to movement to the operating table whereupon more precise movement of the robot arm will be performed for alignment of the trajectory of the end effector (surgical tool holder).

In some implementations, the surgical system includes a surgical robot 102, a tracking detector 108 that captures the position of the patient and different components of the surgical robot 102, and a display screen 110 that displays, for example, real time patient data and/or real time surgical robot trajectories.

In some implementations, when the surgical robot 102 is powered on, robot 102 switches from the standby configuration to another configuration, e.g., a preparation configuration. In some implementations, preset positions of the robotic arm and the arrangement of each moveable portion of the robotic arm of surgical robot 102 may be stored in a memory of the surgical system.

In some implementations, the mobile cart includes a power source for powering the robotic system, including, for example, the actuator. The power source may include a battery and/or a battery backup. In some implementations, the mobile cart is charged and/or powered by an electrical socket in the operating room. The mobile cart may be capable of being powered by a battery on the cart and/or via an electrical outlet. In some implementations, power is provided via an electrical outlet during the surgical procedure. A battery may be used to provide power to the system when the system is being moved or in case of a power cut.

In some implementations, different elements of the surgical system work in tandem by communicating with each other wirelessly. In some implementations, a tracking detector 108 monitors the location of patient 104 and the surgical robot 102. The tracking detector may be a camera, a video camera, an infrared detector, field generator and sensors for electro-magnetic tracking or any other motion detecting apparatus. In some implementation, based on the patient and robot position, the display screen displays a projected trajectory and/or a proposed trajectory for the robotic arm of robot 102 from its current location to a patient operation site. By continuously monitoring the patient and robotic arm positions, using tracking detector 108, the surgical system can calculate updated trajectories and visually display these trajectories on display screen 110 to inform and guide surgeons and/or technicians in the operating room using the surgical robot. In addition, in certain embodiments, the surgical robot 102 may also change its position and automatically position itself based on trajectories calculated from the real time patient and robotic arm positions captured using the tracking detector 108. For instance, the trajectory of the end-effector can be automatically adjusted in real time to account for movement of the vertebrae or other part of the patient during the surgical procedure.

For safety reasons, the mobile cart is provided with a stabilization system that may be used during a surgical procedure performed with a surgical robot. The stabilization mechanism increases the global stiffness of the mobile cart relative to the floor in order to ensure the accuracy of the surgical procedure.

Figure 2A:
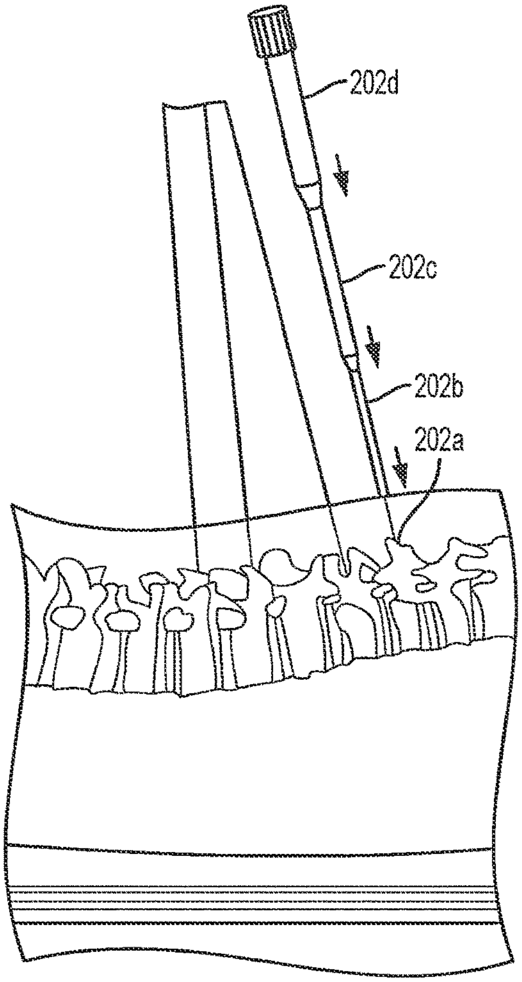
FIGS. 2A-B are illustrations of an example set of dilators used for performing a minimally invasive surgical procedure.
Figure 2B:
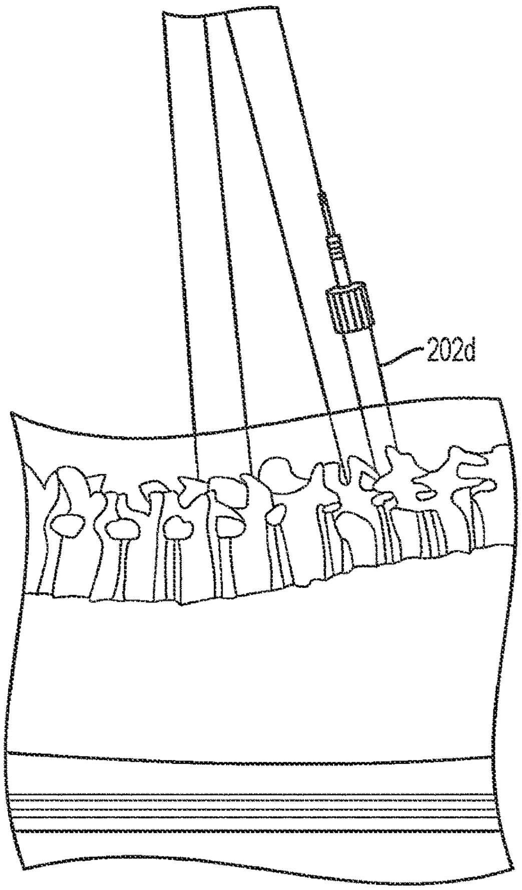

FIGS. 2A-B are illustrations of an example set of dilators 202 used for performing a minimally invasive surgical procedure. Dilators 202 may be used to achieve a working channel for surgical instruments. The dilators may be inserted manually by a surgeon one by one until the surgeon obtains the required diameter of the working channel. For example, a first dilator 202*a* may be inserted at the access point. The first dilator 202 may be a hollow tube-like device (similar to the other dilators 202*b-d*) or it may be a solid tube-like device for marking the access point. The second dilator 202*b* maybe added over the first dilator 202*a*. Similarly, the third dilator 202*c* may be added over the second dilator 202*b* to further increase the size of the working channel. Each dilator added after the first dilator 202*a* increases the size of the working channel. In this example, the fourth dilator 202*d* is added over the third dilator 202*c*. In some implementations, dilators may be removed after the next dilator is added. For example, the second dilator 202*b* may be removed after the third dilator 202*c* is added. In some implementations, dilators may be removed after the last dilator is added. For example, previously added dilators may be removed after the last dilator 202*d* is added, thereby leaving a working channel the diameter of the forth dilator 202*d*.

Figure 3:
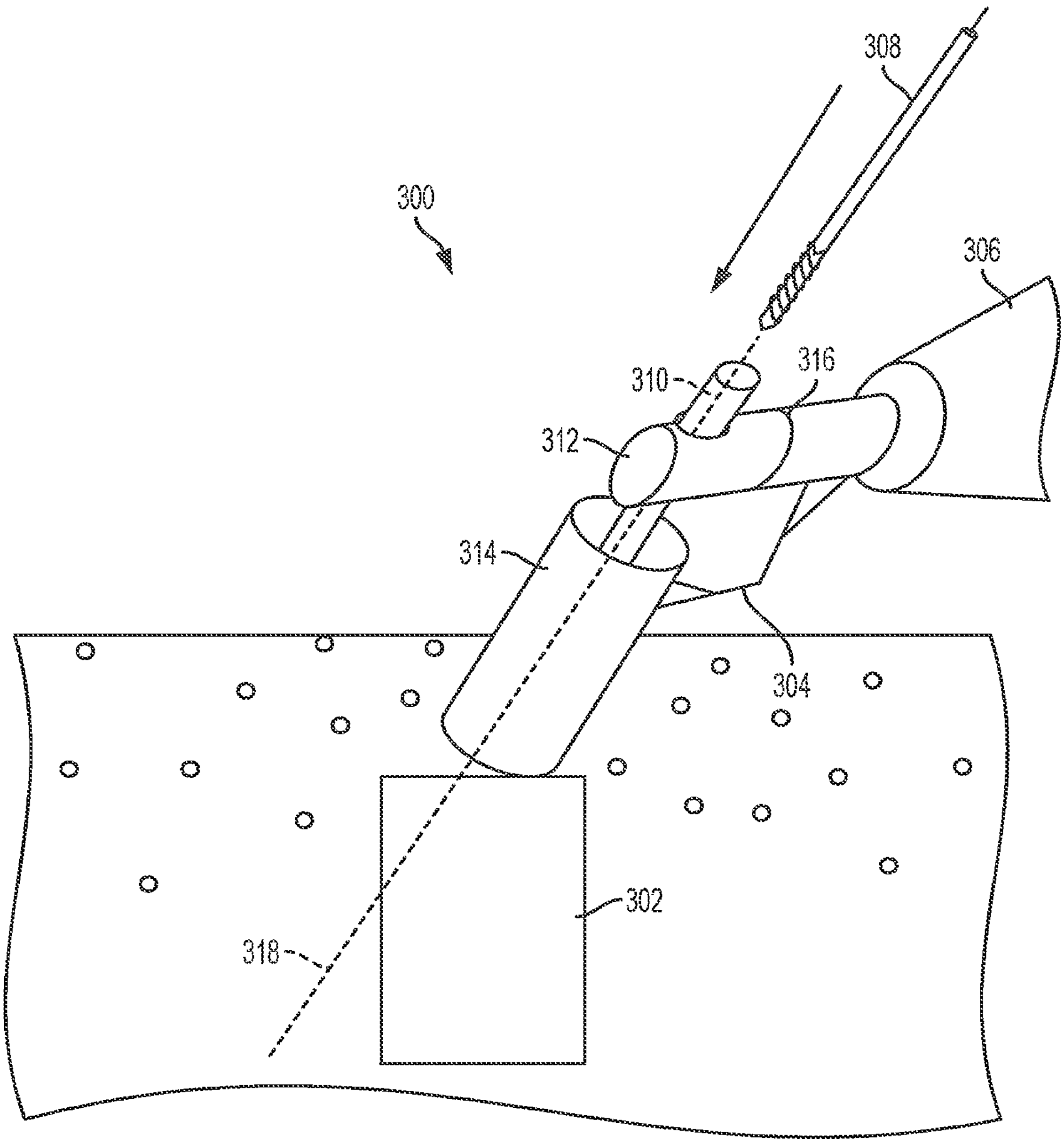
FIG. 3 is an illustration of an example robotic surgical system using a dilator.

The dilators may be used with a robotic surgical system, for example, as shown in FIG. 3. FIG. 3 is an illustration of an example robotic surgical system 300 using a dilator 314. The surgeon may manually obtain access to the vertebrae 302 through the skin and muscles. After applying the dilators as described in relation to FIGS. 2A-B, the internal dilators may be removed, leaving the largest one 314. The robot 306 may be moved closer to the patient and attached to the dilator 314 using the dilator fixation 304. In some implementations, a tool guide 310 held by a tool holder 312 fits inside the dilator 314. The tool guide 310 may be used to guide a surgical instrument 308 to access the vertebrae 302 via the working channel formed by the dilator 314. For example, the tool guide 310 may be used to prepare a hole in vertebrae of a patient. The tool holder 312 may be attached to the may be attached to the robot 306 via a tool holder attachment 316. In some implementations, the dilator 314 itself acts as a tool guide.

In some implementations, standard dilators may be used with the robotic surgical system to provide a precise solution to guide surgical tools. For example, in contrast to surgeries using passive arms to hold the dilator, the dilator may be held by the robotic surgical system and the dilator may be automatically repositioned in response to the surgeon changing the trajectory 318.

A manipulator of the robotic surgical system is configured to allow robotically-assisted or unassisted positioning and/or movement of the dilator attached to the end effector (e.g., the last added dilator) by a user with at least four degrees of freedom to align an axis defined by the dilator attached to the end effector with respect to the vertebrae. The robotic arm is configured to be maneuvered to a desired position to align an axis defined by the surgical instrument guide at a desired trajectory in relation to the vertebrae. The dilator connected to the end effector of the robotic arm is automatically positioned as the robotic arm is maneuvered to adjust to the desired trajectory. Adjustment of the manipulator automatically adjusts an angle and/or position of the attached dilator with respect to the vertebrae and aligns an axis defined by the attached dilator with a desired trajectory during a surgical procedure without removal of the attached dilator from the patient tissue during the repositioning.

Figure 4:
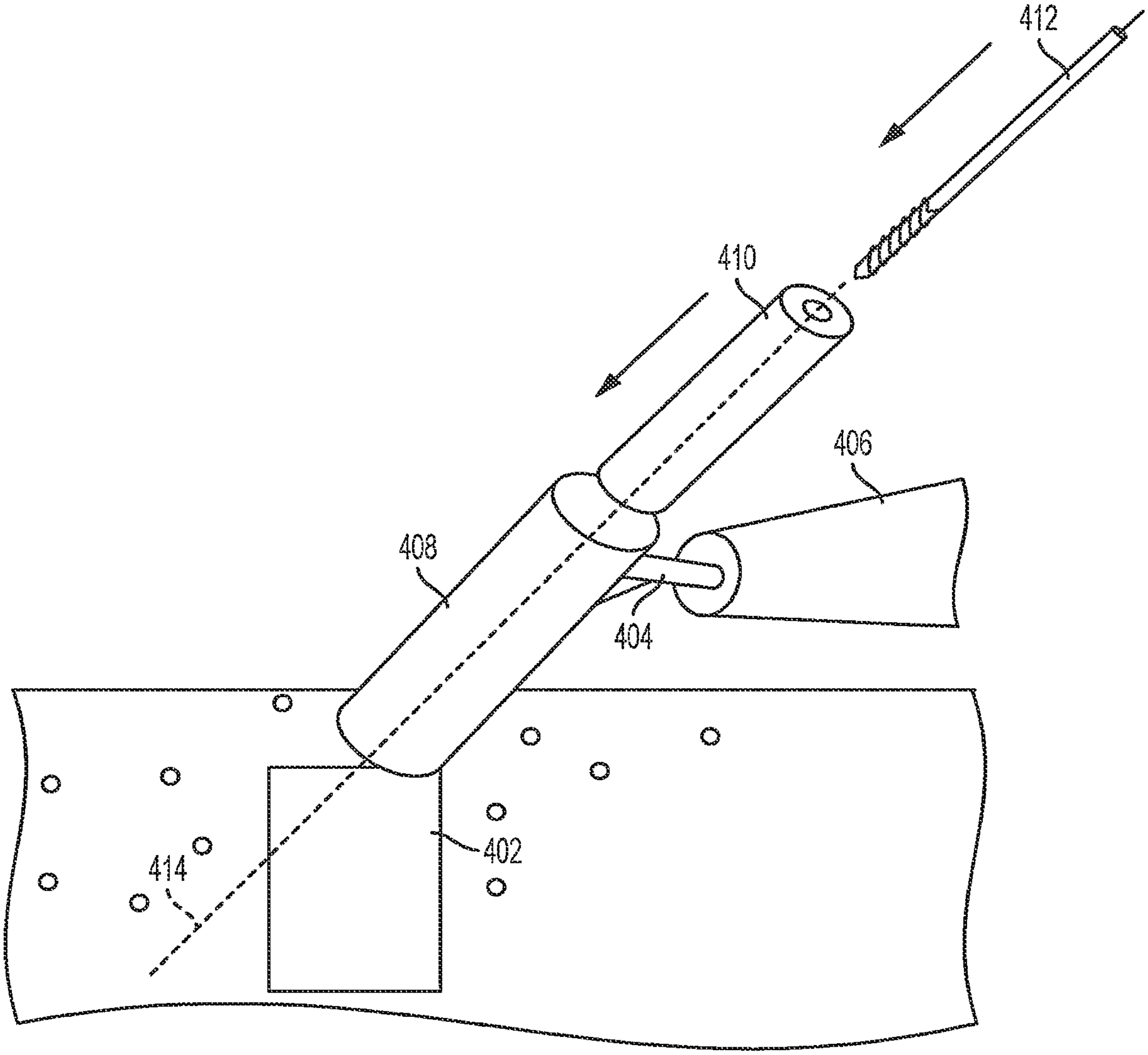
FIG. 4 is an illustration of an example robotic surgical system for performing minimally invasive surgery using a guided dilator.

FIG. 4 is an illustration of an example robotic surgical system for performing a minimally invasive surgery using a guided dilator. The surgeon may manually obtain access to the vertebrae 402 through the skin and muscles. After applying the dilators as described in relation to FIGS. 2A-B, the internal dilators may be removed, leaving the largest one 408. The robot 406 may be moved closer to the patient and attached to the dilator 408 using the dilator fixation 404. The dilator 408 is designed to guide a surgical tool 412. A dilator adapter 410 may be used to allow different size tools to be used with the dilator 408.

In some implementations, standard dilators may be used with the robotic surgical system to provide a precise solution to guide surgical tools. For example, in contrast to surgeries using passive arms to hold the dilator, the dilator may be held by the robotic surgical system and the dilator may be automatically repositioned in response to the surgeon changing the trajectory 414.

Figure 5:
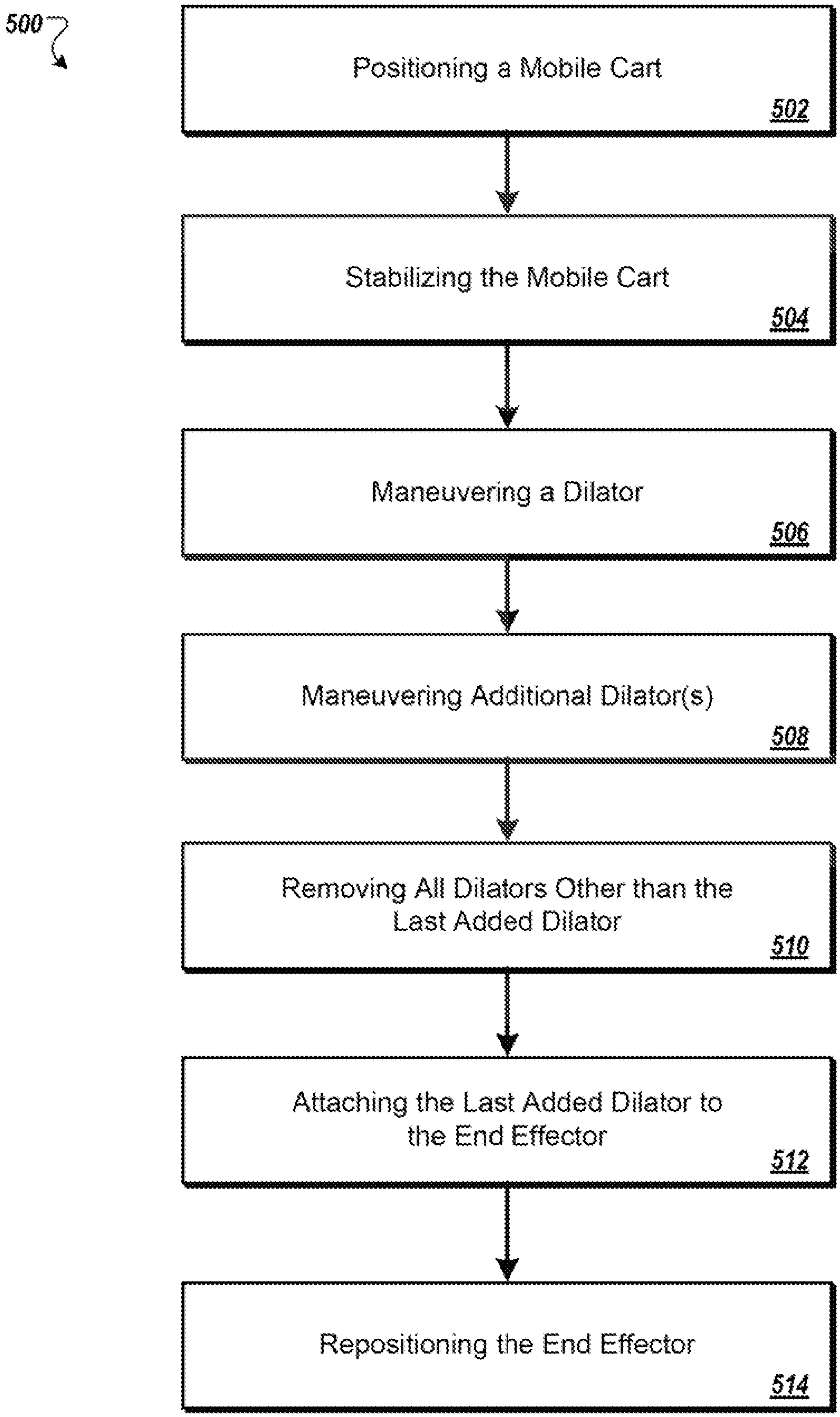
FIG. 5 is a flowchart of an example method of performing minimally invasive spinal surgery with a robotic surgical system.

FIG. 5 is a flowchart of an example method 500 of performing minimally invasive spinal surgery with a robotic surgical system. In some implementations, the method may include positioning a mobile cart (502) transporting a robotic surgical system. The robotic surgical system may include a robotic arm in proximity to an operating table. The robotic arm may have an end effector. After positioning the mobile cart, the mobile cart may be stabilized (504).

The method 500 may include maneuvering a dilator to access a vertebrae of a patient through the patient's muscles and skin (506). The dilator may define a working channel for accessing the vertebrae. Additional dilators may be placed over earlier placed dilator(s) (508) to increase the size of the working channel. All dilators except the last added dilator may be removed (510) thereby leaving a working channel of a desired diameter for the surgery.

For example, a second dilator may be maneuvered to slide over the dilator. The second dilator may be sized and shaped to slide over the dilator and increase the size of the working channel. After positioning the second dilator over the dilator (and/or after positioning one or more subsequent dilators over the preceding dilators), the dilator (and/or other dilators except the final added dilator) may be removed from the patient, thereby leaving the last added dilator.

The method 500 may include attaching a dilator to the end effector of the robotic arm using a dilator fixator (512). In some implementations, the dilator attached (or to be attached) to the end effector is the dilator with largest circumference. Following attachment of the dilator to the end effector, the end effector may be repositioned to adjust the angle and/or position of the attached dilator with respect to the vertebrae (514). The robotic arm may be maneuvered to a desired position to align an axis defined by the surgical instrument guide at a desired trajectory in relation to the vertebrae. This causes the dilator connected to the end effector of the robotic arm to be automatically positioned as the robotic arm is maneuvered to adjust to the desired trajectory.

In some implementations, a surgical instrument guide is placed inside of the dilator attached (or to be attached) to the end effector. The surgical instrument guide (e.g., drill bit guide, tap guide, screwdriver guide, screw guide, awl guide, and implant guide) is sized and shaped to fit at least partially inside the dilator along an axis defined by the dilator and is configured to hold and/or restrict movement of a surgical instrument (e.g., drill bit, pedicle finder, screw-based implant, awl, surface-pointing device, screw based implant, screw driver, tap, implants, implants with extenders, or other similar instruments) therethrough. The surgical instrument may be, for example, a tap such as the StealthStation® CR Horizon Legacy Taps from Medtronic, Inc. of Minneapolis, MN or a universal surgical tools system (e.g., Medtronic's NavLock system). In some implementations, the dilator itself is used as a surgical instrument guide. The dilator may be configured to hold and/or restrict movement of a surgical instrument. Dilator adapters may be used to allow different size instruments to be guided by the dilator.

Figure 6:
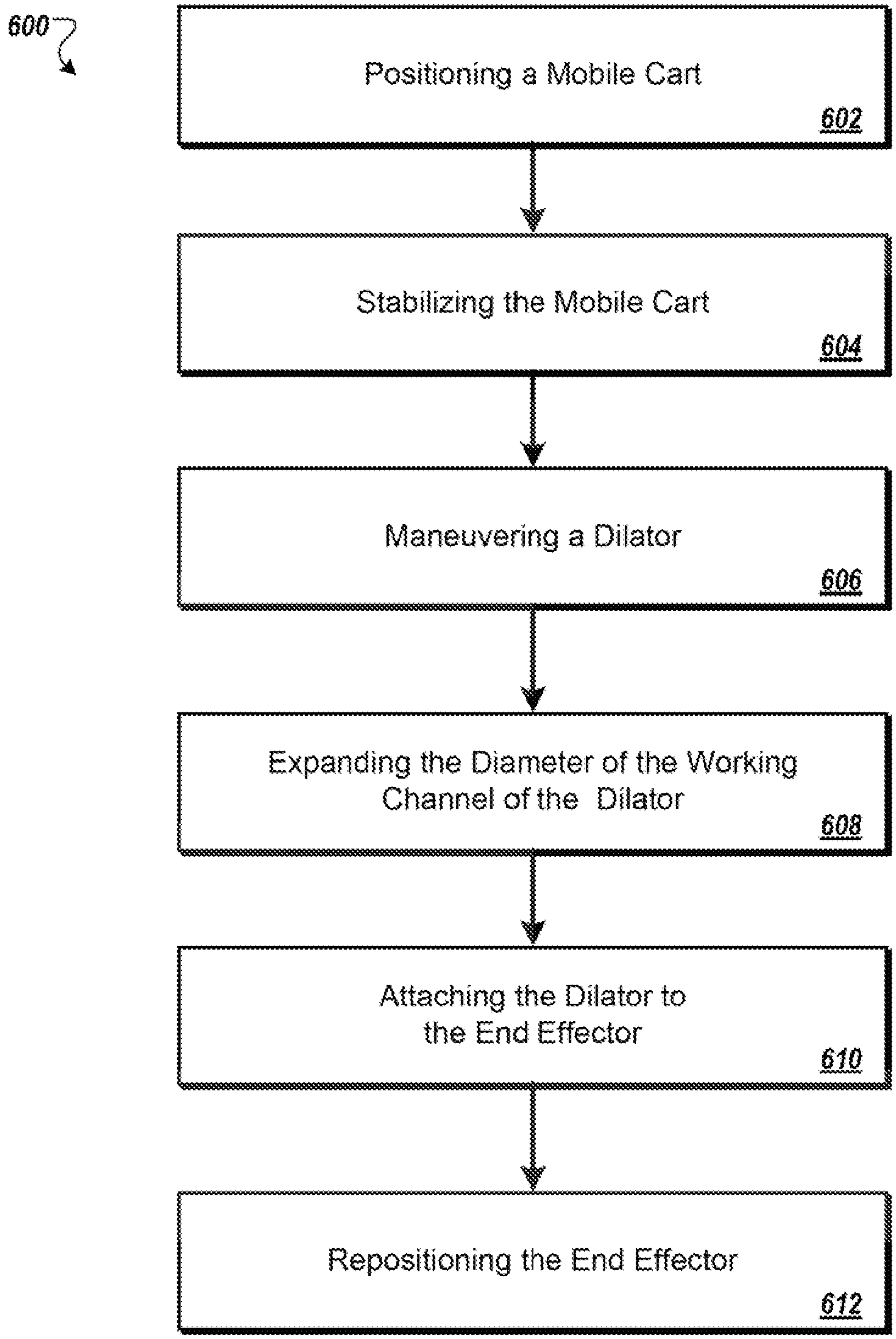
FIG. 6 is a flowchart of an example method for performing minimally invasive surgery using minimally invasive surgical techniques.

FIG. 6 is a flowchart of an example method 600 for performing minimally invasive surgery. In some implementations, the method may include positioning a mobile cart (602) transporting a robotic surgical system. The robotic surgical system may include a robotic arm in proximity to an operating table. The robotic arm may have an end effector. After positioning the mobile cart, the mobile cart may be stabilized (604).

The method 600 may include maneuvering a dilator to access a vertebrae of a patient through the patient's muscles and skin (606). The dilator may define a working channel for accessing the vertebrae. The diameter of the working channel of the dilator may be expanded (608). For example, the dilator may be configured such that the diameter of the dilator may be increased. Thus, the size of the working channel may be increased without the use of multiple dilators.

The method 600 may include attaching the dilator to the end effector of the robotic arm using a dilator fixator (610). Following attachment of the dilator to the end effector, the end effector may be repositioned to adjust the angle and/or position of the attached dilator with respect to the vertebrae (612).

Figure 7:
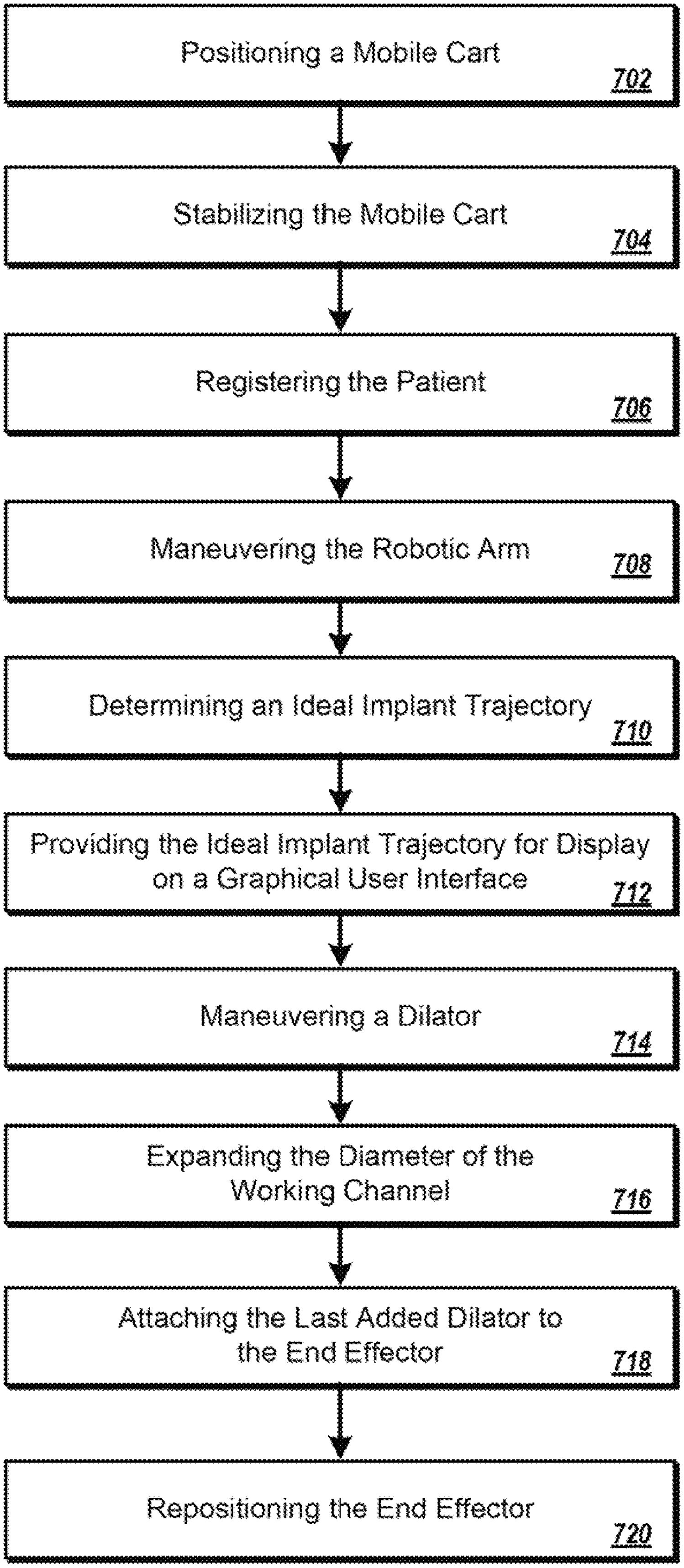
FIG. 7 is a flowchart of an example method for performing minimally invasive surgery using minimally invasive surgical techniques.

FIG. 7 is a flowchart of an example method 700 for performing minimally invasive surgery using minimally invasive surgical techniques. In some implementations, the method may include positioning a mobile cart (702) transporting a robotic surgical system. The robotic surgical system may include a robotic arm in proximity to an operating table. The robotic arm may have an end effector. After positioning the mobile cart, the mobile cart may be stabilized (704).

The method 700 may include registering the patient (706). Registering the patient may include identifying the transformation between the actual patient anatomy and one or more medical images. Registering the patient may include identifying a correlation between the surgical anatomy of the patient in the "real world" and a medical image (e.g., an image acquisition during surgery). Registration may also be accomplished using co-registration (e.g., former studies). The robotic arm may be maneuvered towards the vertebrae on which the surgeon will operate (708). In some implementations, the robotic surgical system will recognize the vertebra on which the surgeon wishes to operate as the robotic arm is maneuvered towards the vertebra. A processor of a computing device may determine an ideal implant trajectory (710). The system allows for a desired trajectory (e.g., for a drill guide during spinal surgery) to be set in a variety of manners based on the circumstances of the surgery. For example, some surgical procedures are planned pre-operatively with the surgeon defining the desired position of an implant using imaging technology, such as CT images (e.g., 3D CT images). The desired position of the implant may also be determined and proposed by the system. In the operating room the surgeon may be guided by the robotic system (e.g., robotic guidance of the surgical tools) to accurately execute the planning.

The ideal implant trajectory may be displayed on a graphical user interface for review by the surgeon (712). The surgeon may adapt the ideal implant trajectory if needed using hands-on planning. The surgeon acknowledges the ideal implant trajectory or the adapted trajectory thereby causing the acknowledged trajectory to be stored as the desired trajectory.

The method 700 may include maneuvering a dilator to access a vertebrae of a patient through the patient's muscles and skin (714). The dilator may define a working channel for accessing the vertebrae. The diameter of the working channel may be expanded (716) using the techniques as described in relation to FIGS. 5 and 6. The method 700 may include attaching the dilator to the end effector of the robotic arm using a dilator fixator (718). Following attachment of the dilator to the end effector, the end effector may be repositioned to adjust the angle and/or position of the attached dilator with respect to the vertebrae (720).

Having described various embodiments of the disclose technology, it will now become apparent to one of skill in the art that other embodiments incorporating the concepts may be used. It is felt, therefore, that these embodiments should not be limited to the disclosed embodiments, but rather should be limited only by the spirit and scope of the following claims.

Figure 8:
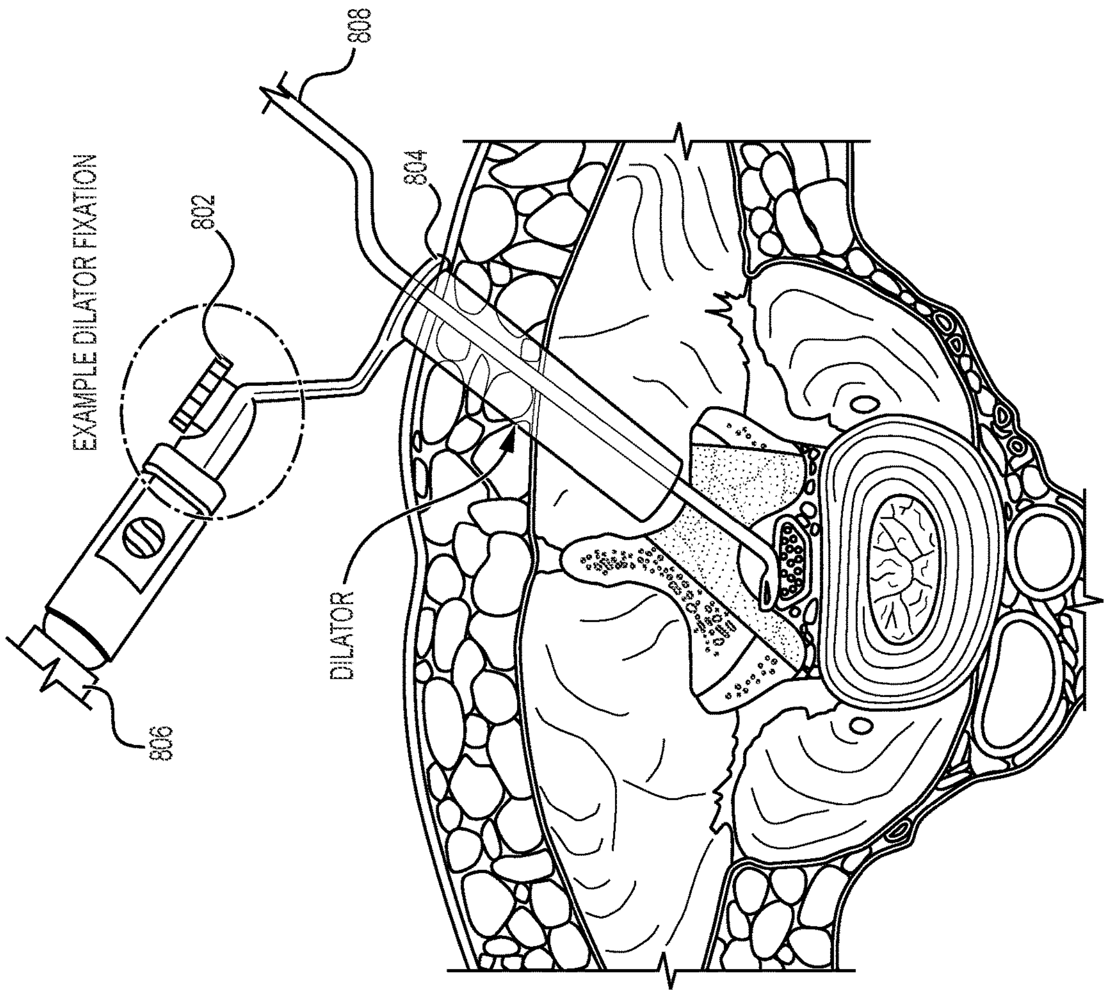
FIG. 8 is an illustration of an example dilator fixation for attaching a dilator to a robotic arm.

FIG. 8 is an illustration of an example dilator fixation 802 for attaching a dilator 804 to a robotic arm 806. The dilator fixation 802 may be mechanically coupled to the robotic arm 806 such that the dilator fixation is rigidly coupled to the robotic arm 806. For example, the dilator fixation 802 maybe bolted to the robotic arm 806 such that the dilator fixation 802 will not move relative to the robotic arm 806 thereby allowing the robot to always knows the position of the dilator fixation 802. The dilator fixation 802 may provide a quick-release mechanism to rigidly secure the dilator or surgical instrument guide 804 to the robotic arm 806. In some implementations, the dilator or surgical instrument guide 804 and dilator fixation 802 are formed as one piece and attached to the robotic arm 806 via a bolt, screw, or quick-release mechanism. The attachment system may be designed such that the dilator or surgical instrument guide 804 may be removed quickly and easily (e.g., toollessly).

Figure 9A:
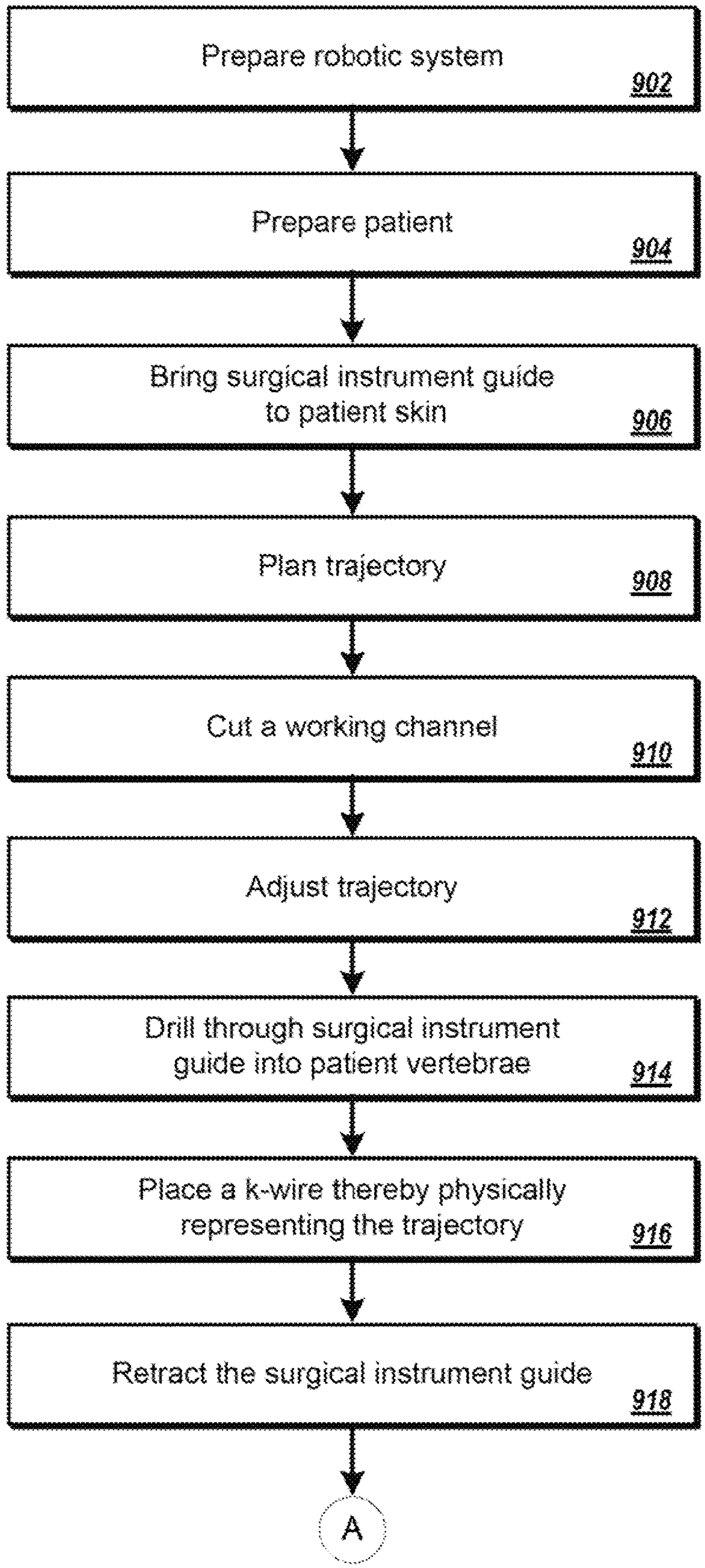
FIGS. 9A-B illustrate a block diagram of an example method of performing minimally invasive spinal surgery with a robotic surgical system.
Figure 9B:
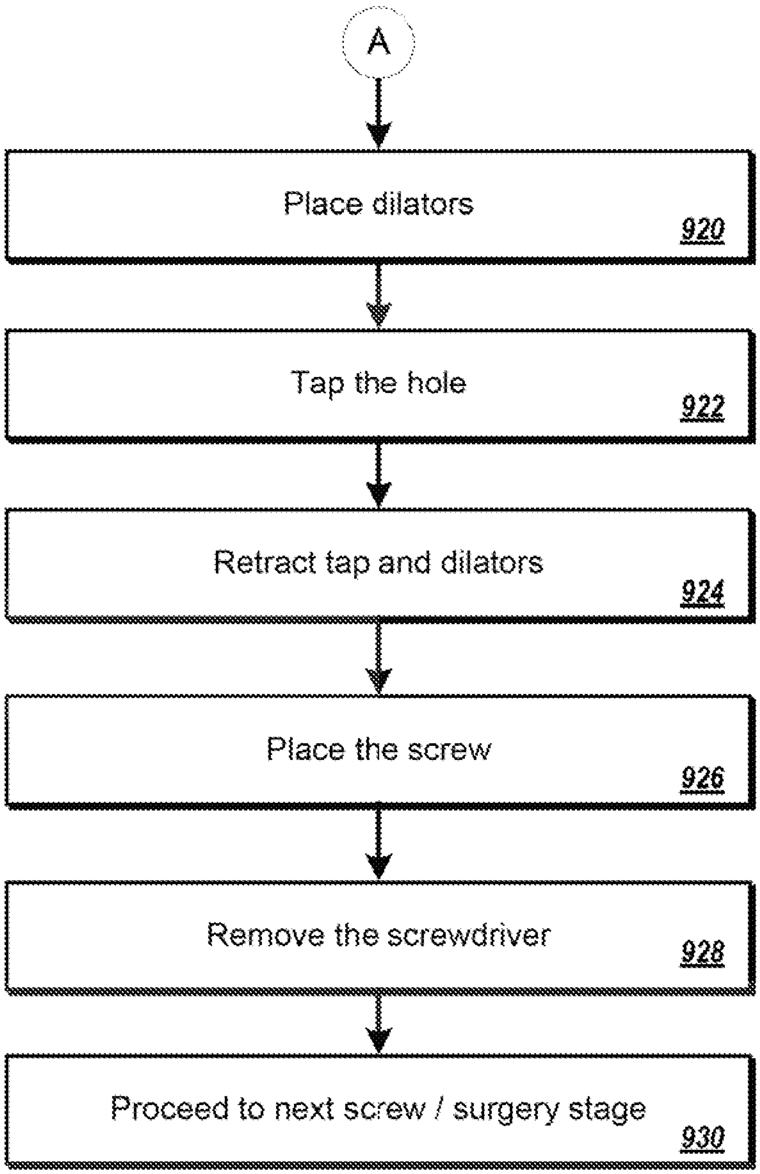

FIGS. 9A-B are a flowchart of an example method for performing minimally invasive spinal surgery with a robotic surgical system. The robotic system is prepared and brought to the operating table in accordance with the methods of the present disclosure (902). The patient is prepared for the surgery (904). The surgeon brings the surgical instrument guide to the region of interest above the anatomy that will be operated on (906). Once in position and before incision, the surgeon plans a trajectory (908). The trajectory is set by maneuvering the surgical instrument guide by the surgeon. The surgeon, in certain embodiments, may physically grab the surgical instrument guide or a handle on the end effector and move the surgical instrument guide until it is aligned with the desired trajectory (e.g., as determined by the surgeon). The robot can control the rate at which the surgeon moves the surgical instrument guide to assist the surgeon in precise movements, however, in certain embodiments, the surgeon may freely move the surgical instrument guide to align it with the desired trajectory.

In some implementations, the surgeon observes the current trajectory on a navigation screen. In certain embodiments, a composite image comprising a visual representation of the trajectory superimposed with a medical image of the patient's vertebrae is displayed on the navigation screen.

After setting a trajectory the surgeon cuts through the patient's muscle and skin thereby exposing the vertebrae (910). In some embodiments, once a trajectory has been set, the motion of the surgical instrument guide is constrained to the trajectory.

The surgical instrument guide is moved to the surface of the vertebrae along the trajectory. At this point, the surgeon may readjust the trajectory (e.g., fine tune the trajectory) right at the surface of the vertebrae (912). In some embodiments, the surgeon decouples translation movement (for finding the entry point) from rotation movement (i.e., around the tip of the surgical instrument guide or other tool defining trajectory direction). The surgeon then drills, through the surgical instrument guide, a hole into the vertebrae of the patient (914)

The surgeon places a k-wire into the hole (916). In certain embodiments, the k-wire (e.g., a flexible k-wire), due to sticking out of and being constrained by the previously drilled hole, provides a physical representation of the trajectory. This allows the surgeon to physically preserve the trajectory for future retrieval. In some embodiments, the surgeon removes a portion of the surgical instrument guide (e.g., an outer or inner tube of the surgical instrument guide) to change the diameter of the guide for the drilling and k-wire steps. In certain embodiments, a k-wire is not used and the trajectory is instead preserved within the memory of a computing device. The surgeon then retracts the surgical instrument guide (918). In some embodiments, the surgeon can reverse the motion of the surgical instrument guide along the trajectory, thereby decreasing incidental stresses on the k-wire. In certain embodiments, the k-wire is a flexible k-wire, which assists in removal of the surgical guide. The flexible k-wire allows the k-wire to bend while the surgical instrument guide is retracted, and the k-wire returns to the trajectory position once the surgical instrument guide has been fully retracted.

After or prior to insertion of the k-wire, the surgeon may expand the working channel by placing progressively larger dilators around the k-wire and/or surgical instrument guide (920), as described in the present disclosure. The surgeon then taps the hole in the vertebrae sliding the tap along (e.g., over) the k-wire (922). In certain embodiments, the tapping step may be omitted. In other embodiments, if a k-wire is not used, the surgeon can locate the hole by retrieving the trajectory stored in computer memory and displaying the trajectory to the surgeon on the navigation display. At this stage, the dilators may be removed (924), or they may be removed at any other convenient point (e.g., any time after drilling). The screw is then placed by sliding the screw driver along (e.g., over) the k-wire (926). In certain embodiments, if a k-wire is not used, the surgeon can locate the hole by retrieving the trajectory stored in computer memory and displaying the trajectory to the surgeon on the navigation display. In some embodiments, the screw comprises an extensor attached to the back of the screw. This simplifies finding the screw later when placing rods. The screwdriver is removed from the patient while the screw remains in the patient (928). If desired, additional screws may be inserted by repeating the procedure at the appropriate location (930).

Figure 10:
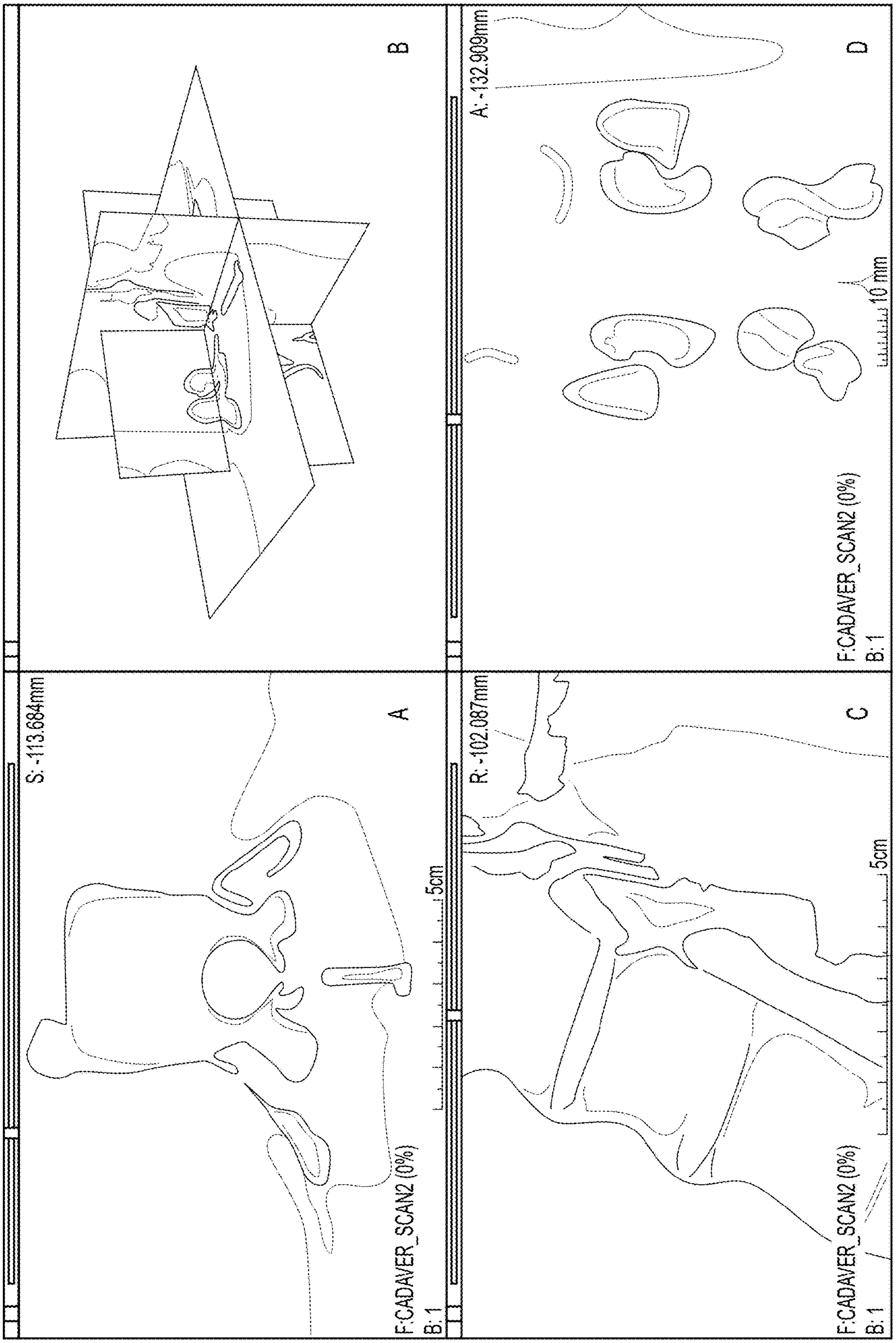
FIG. 10 is an intraoperative medical image showing a vertebrae before placing screws therein.
Figure 11:
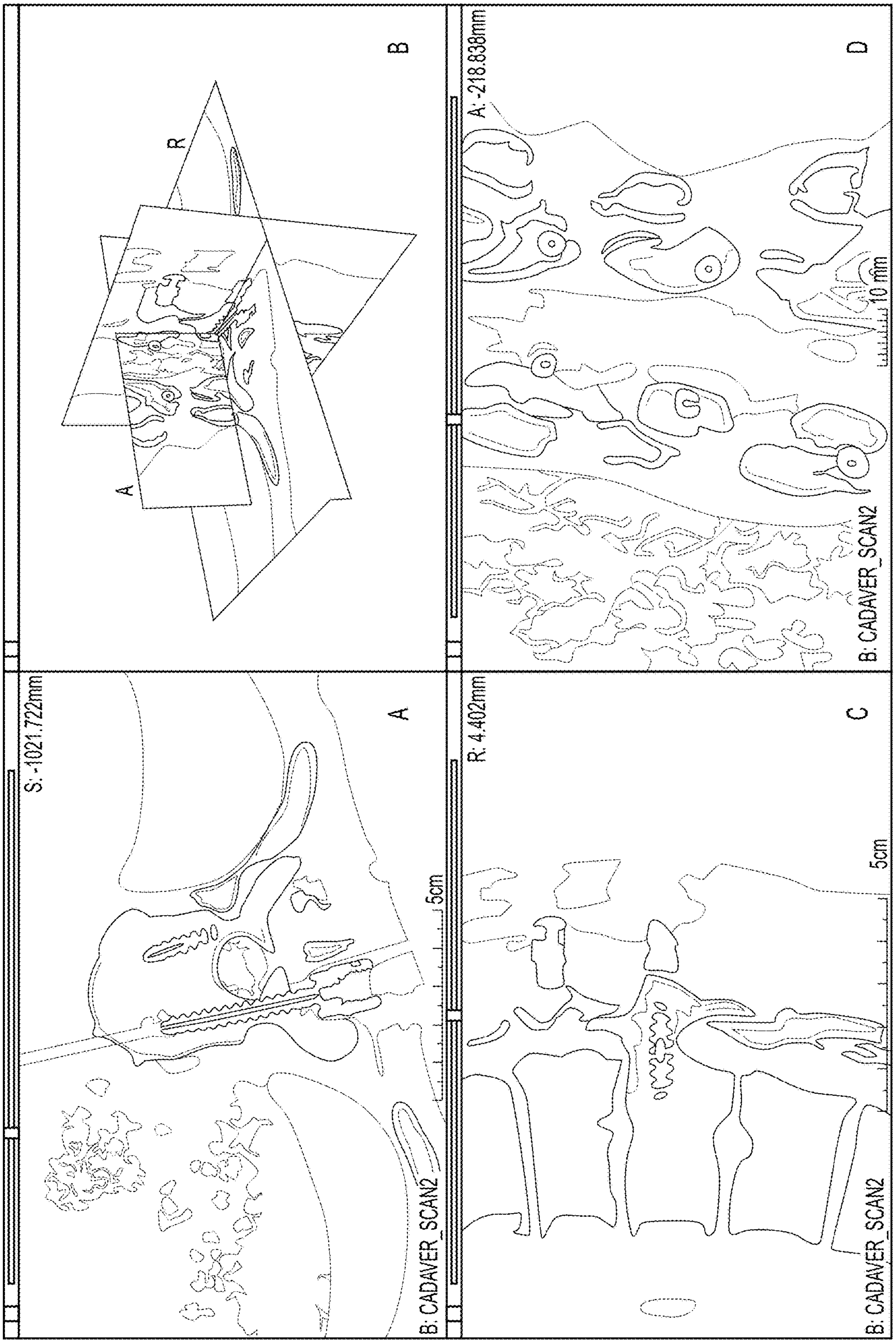
FIG. 11 is a postoperative medical image showing vertebrae with screws in place.
Figure 12:
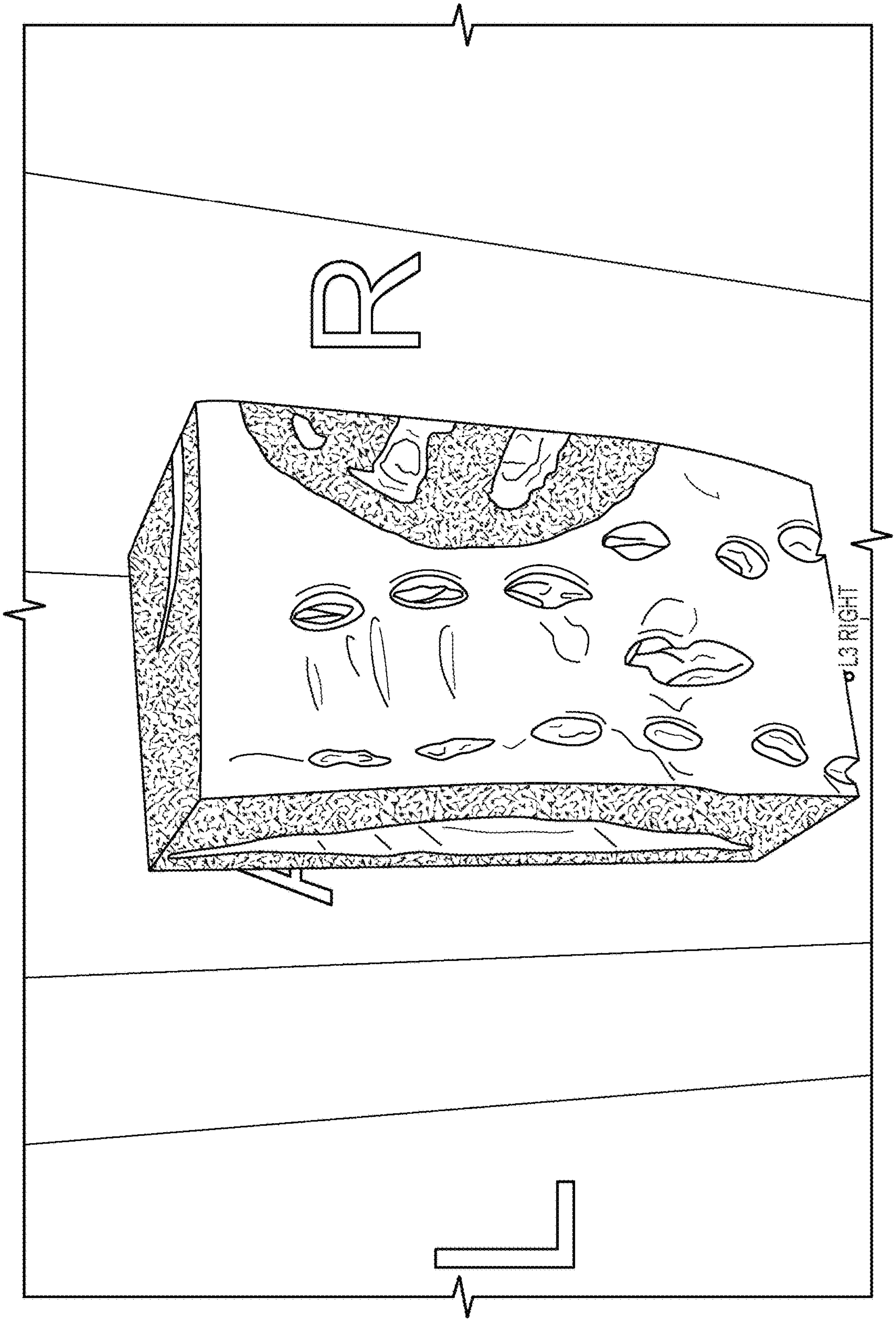
FIG. 12 is a volumetric medical image showing small skin incisions after percutaneous screw placement.
Figure 13:
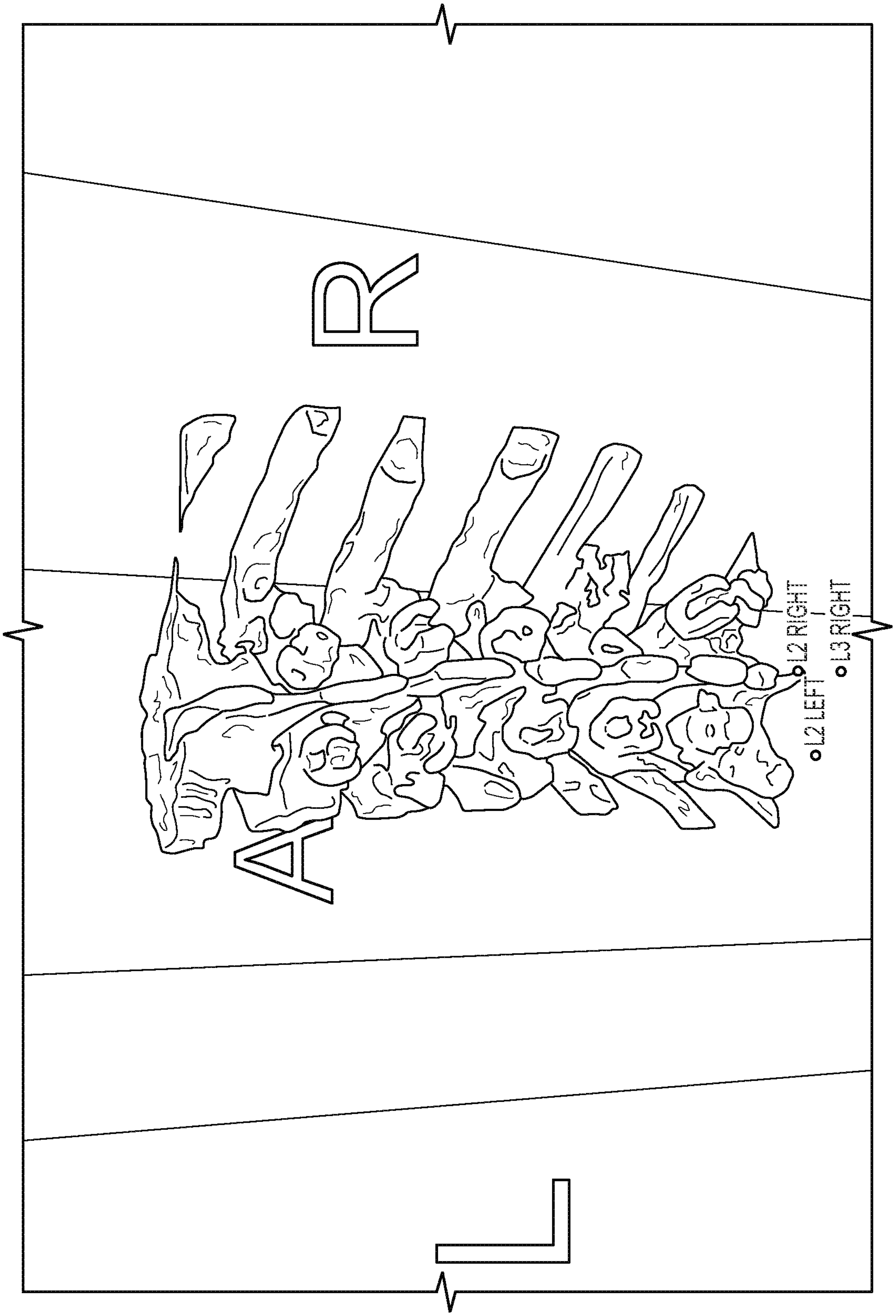
FIG. 13 is a volumetric medical image showing screws placed in the vertebrae.

FIG. 10 is an intraoperative medical image showing a vertebrae before placing the screw. FIG. 11 is a postoperative medical image showing vertebrae with screws in place. FIG. 12 is a volumetric medical image showing small skin incisions after percutaneous screw placement, according to an embodiment of the present disclosure. FIG. 13 is a volumetric medical image showing screws placed in the vertebrae, according to an embodiment of the present disclosure.

Figure 14:
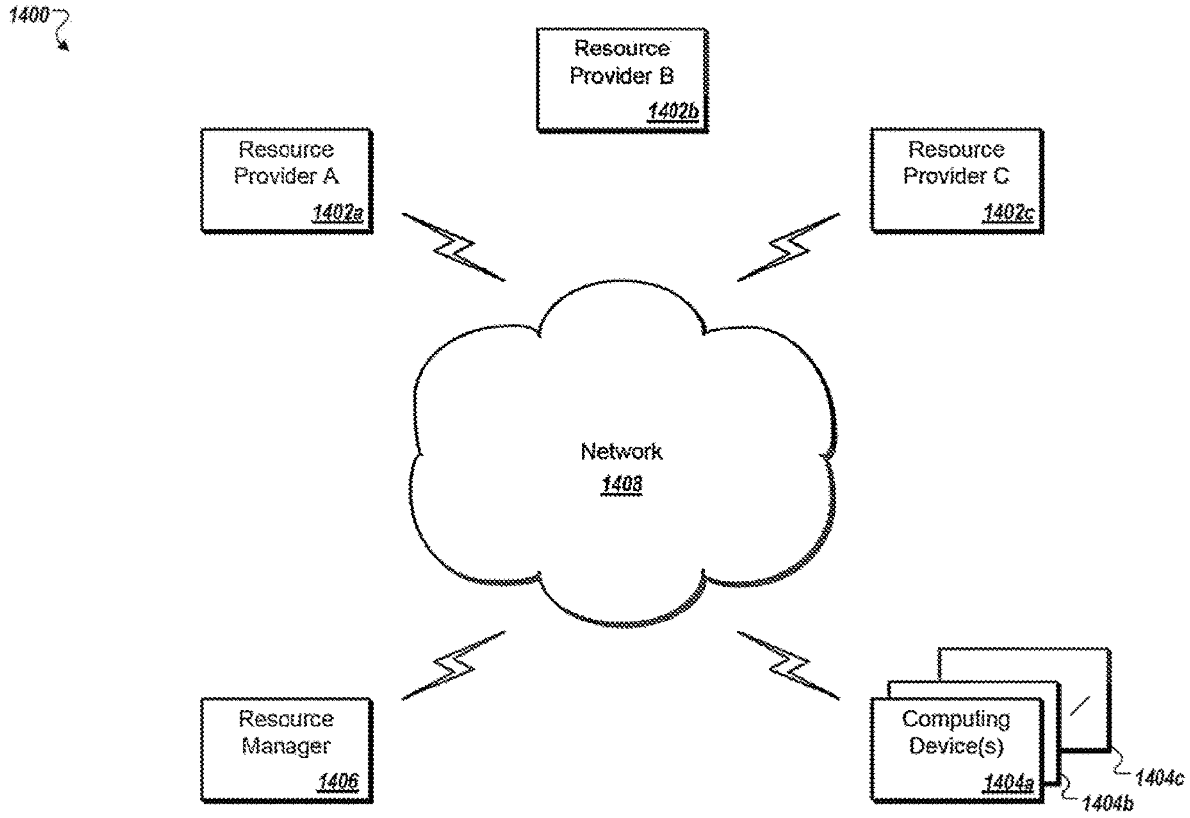
FIG. 14 illustrates a block diagram of an exemplary cloud computing environment.

As shown in FIG. 14, an implementation of a network environment 1400 for use in performing minimally invasive surgical techniques is shown and described. In brief overview, referring now to FIG. 14, a block diagram of an exemplary cloud computing environment 1400 is shown and described. The cloud computing environment 1400 may include one or more resource providers 1402*a*, 1402*b*, 1402*c* (collectively, 1402). Each resource provider 1402 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 1402 may be connected to any other resource provider 1402 in the cloud computing environment 1400. In some implementations, the resource providers 1402 may be connected over a computer network 1408. Each resource provider 1402 may be connected to one or more computing device 1404*a*, 1404*b*, 1404*c* (collectively, 1404), over the computer network 1408.

The cloud computing environment 1400 may include a resource manager 1406. The resource manager 1406 may be connected to the resource providers 1402 and the computing devices 1404 over the computer network 1408. In some implementations, the resource manager 1406 may facilitate the provision of computing resources by one or more resource providers 1402 to one or more computing devices 1404. The resource manager 1406 may receive a request for a computing resource from a particular computing device 1404. The resource manager 1406 may identify one or more resource providers 1402 capable of providing the computing resource requested by the computing device 1404. The resource manager 1406 may select a resource provider 1402 to provide the computing resource. The resource manager 1406 may facilitate a connection between the resource provider 1402 and a particular computing device 1404. In some implementations, the resource manager 1406 may establish a connection between a particular resource provider 1402 and a particular computing device 1404. In some implementations, the resource manager 1406 may redirect a particular computing device 1404 to a particular resource provider 1402 with the requested computing resource.

Figure 15:
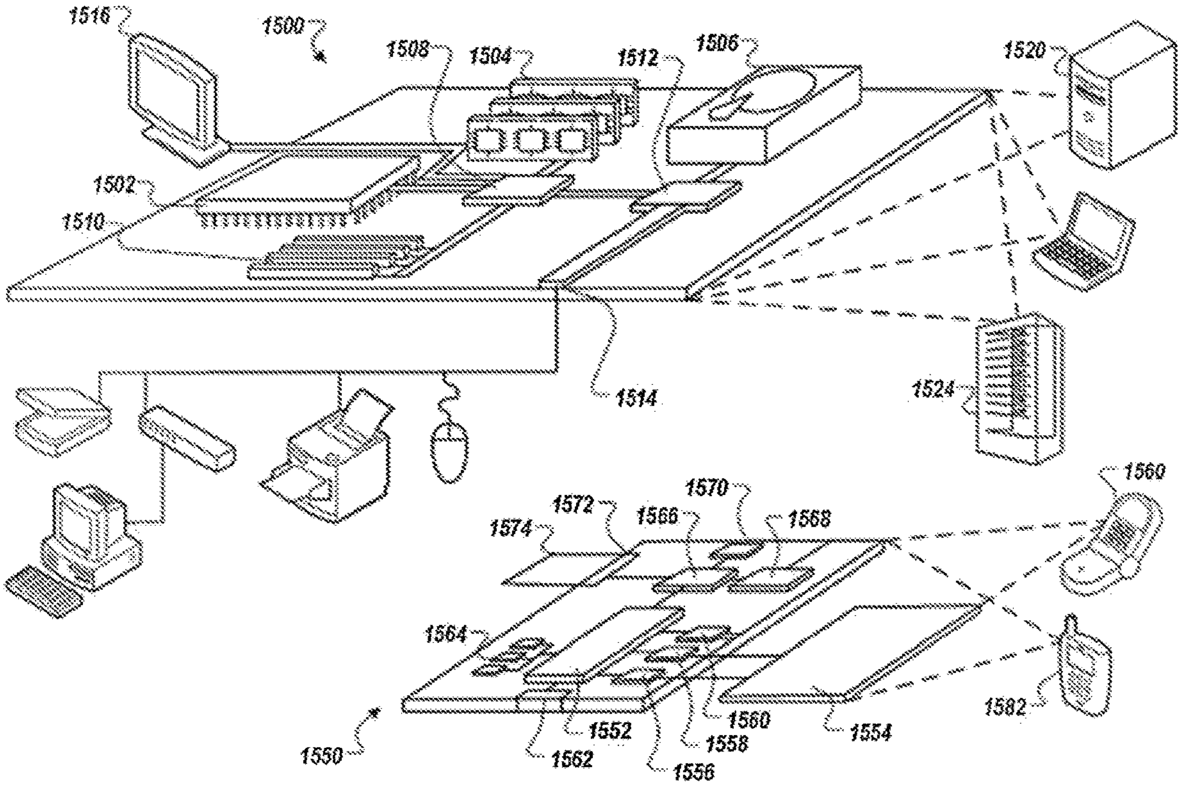
FIG. 15 is a block diagram of a computing device and a mobile computing device.

FIG. 15 shows an example of a computing device 1500 and a mobile computing device 1550 that can be used to implement the techniques described in this disclosure. The computing device 1500 is intended to represent various forms of digital computers, such as laptops, desktops, workstations, personal digital assistants, servers, blade servers, mainframes, and other appropriate computers. The mobile computing device 1550 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 1500 includes a processor 1502, a memory 1504, a storage device 1506, a high-speed interface 1508 connecting to the memory 1504 and multiple high-speed expansion ports 1510, and a low-speed interface 1512 connecting to a low-speed expansion port 1514 and the storage device 1506. Each of the processor 1502, the memory 1504, the storage device 1506, the high-speed interface 1508, the high-speed expansion ports 1510, and the low-speed interface 1512, are interconnected using various busses, and may be mounted on a common motherboard or in other manners as appropriate. The processor 1502 can process instructions for execution within the computing device 1500, including instructions stored in the memory 1504 or on the storage device 1506 to display graphical information for a GUI on an external input/output device, such as a display 1516 coupled to the high-speed interface 1508. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 1504 stores information within the computing device 1500. In some implementations, the memory 1504 is a volatile memory unit or units. In some implementations, the memory 1504 is a non-volatile memory unit or units. The memory 1504 may also be another form of computer-readable medium, such as a magnetic or optical disk.

The storage device 1506 is capable of providing mass storage for the computing device 1500. In some implementations, the storage device 1506 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 1502), perform one or more methods, such as those described above. The instructions can also be stored by one or more storage devices such as computer- or machine-readable mediums (for example, the memory 1504, the storage device 1506, or memory on the processor 1502).

The high-speed interface 1508 manages bandwidth-intensive operations for the computing device 1500, while the low-speed interface 1512 manages lower bandwidth-intensive operations. Such allocation of functions is an example only. In some implementations, the high-speed interface 1508 is coupled to the memory 1504, the display 1516 (e.g., through a graphics processor or accelerator), and to the high-speed expansion ports 1510, which may accept various expansion cards (not shown). In the implementation, the low-speed interface 1512 is coupled to the storage device 1506 and the low-speed expansion port 1514. The low-speed expansion port 1514, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 1500 may be implemented in a number of different forms, as shown in the figure. For example, it may be implemented as a standard server 1520, or multiple times in a group of such servers. In addition, it may be implemented in a personal computer such as a laptop computer 1522. It may also be implemented as part of a rack server system 1524. Alternatively, components from the computing device 1500 may be combined with other components in a mobile device (not shown), such as a mobile computing device 1550. Each of such devices may contain one or more of the computing device 1500 and the mobile computing device 1550, and an entire system may be made up of multiple computing devices communicating with each other.

The mobile computing device 1550 includes a processor 1552, a memory 1564, an input/output device such as a display 1554, a communication interface 1566, and a transceiver 1568, among other components. The mobile computing device 1550 may also be provided with a storage device, such as a micro-drive or other device, to provide additional storage. Each of the processor 1552, the memory 1564, the display 1554, the communication interface 1566, and the transceiver 1568, are interconnected using various buses, and several of the components may be mounted on a common motherboard or in other manners as appropriate.

The processor 1552 can execute instructions within the mobile computing device 1550, including instructions stored in the memory 1564. The processor 1552 may be implemented as a chipset of chips that include separate and multiple analog and digital processors. The processor 1552 may provide, for example, for coordination of the other components of the mobile computing device 1550, such as control of user interfaces, applications run by the mobile computing device 1550, and wireless communication by the mobile computing device 1550.

The processor 1552 may communicate with a user through a control interface 1558 and a display interface 1556 coupled to the display 1554. The display 1554 may be, for example, a TFT (Thin-Film-Transistor Liquid Crystal Display) display or an OLED (Organic Light Emitting Diode) display, or other appropriate display technology. The display interface 1556 may comprise appropriate circuitry for driving the display 1554 to present graphical and other information to a user. The control interface 1558 may receive commands from a user and convert them for submission to the processor 1552. In addition, an external interface 1562 may provide communication with the processor 1552, so as to enable near area communication of the mobile computing device 1550 with other devices. The external interface 1562 may provide, for example, for wired communication in some implementations, or for wireless communication in other implementations, and multiple interfaces may also be used.

The memory 1564 stores information within the mobile computing device 1550. The memory 1564 can be implemented as one or more of a computer-readable medium or media, a volatile memory unit or units, or a non-volatile memory unit or units. An expansion memory 1574 may also be provided and connected to the mobile computing device 1550 through an expansion interface 1572, which may include, for example, a SIMM (Single In Line Memory Module) card interface. The expansion memory 1574 may provide extra storage space for the mobile computing device 1550, or may also store applications or other information for the mobile computing device 1550. Specifically, the expansion memory 1574 may include instructions to carry out or supplement the processes described above, and may include secure information also. Thus, for example, the expansion memory 1574 may be provided as a security module for the mobile computing device 1550, and may be programmed with instructions that permit secure use of the mobile computing device 1550. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier and, when executed by one or more processing devices (for example, processor 1552), perform one or more methods, such as those described above. The instructions can also be stored by one or more storage devices, such as one or more computer- or machine-readable mediums (for example, the memory 1564, the expansion memory 1574, or memory on the processor 1552). In some implementations, the instructions can be received in a propagated signal, for example, over the transceiver 1568 or the external interface 1562.

The mobile computing device 1550 may communicate wirelessly through the communication interface 1566, which may include digital signal processing circuitry where necessary. The communication interface 1566 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 1568 using a radio-frequency. In addition, short-range communication may occur, such as using a Bluetooth®, Wi-Fi™, or other such transceiver (not shown). In addition, a GPS (Global Positioning System) receiver module 1570 may provide additional navigation- and location-related wireless data to the mobile computing device 1550, which may be used as appropriate by applications running on the mobile computing device 1550.

The mobile computing device 1550 may also communicate audibly using an audio codec 1560, which may receive spoken information from a user and convert it to usable digital information. The audio codec 1560 may likewise generate audible sound for a user, such as through a speaker, e.g., in a handset of the mobile computing device 1550. Such sound may include sound from voice telephone calls, may include recorded sound (e.g., voice messages, music files, etc.) and may also include sound generated by applications operating on the mobile computing device 1550.

The mobile computing device 1550 may be implemented in a number of different forms, as shown in the figure. For example, it may be implemented as a cellular telephone 1580. It may also be implemented as part of a smart-phone 1582, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In view of the structure, functions and apparatus of the systems and methods described here, in some implementations, a system and method for performing minimally invasive surgical techniques are provided. Having described certain implementations of methods and apparatus for supporting minimally invasive surgical techniques, it will now become apparent to one of skill in the art that other implementations incorporating the concepts of the disclosure may be used. Therefore, the disclosure should not be limited to certain implementations, but rather should be limited only by the spirit and scope of the following claims.

Throughout the description, where apparatus and systems are described as having, including, or comprising specific components, or where processes and methods are described as having, including, or comprising specific steps, it is contemplated that, additionally, there are apparatus, and systems of the disclosed technology that consist essentially of, or consist of, the recited components, and that there are processes and methods according to the disclosed technology that consist essentially of, or consist of, the recited processing steps.

It should be understood that the order of steps or order for performing certain action is immaterial so long as the disclosed technology remains operable. Moreover, two or more steps or actions may be conducted simultaneously.

The invention claimed is:

1. A robotic surgical system for performing minimally invasive surgery comprising:

a robotic arm with an end effector;

a first dilator to access a vertebrae of a patient through a patient's muscles and skin, wherein the first dilator defines a working channel for accessing the vertebrae;

one or more subsequent dilators sized and shaped to slide over the first dilator and/or one or more of the one or more subsequent dilators, wherein the one or more subsequent dilators comprises a last added dilator configured to be attached to the end effector of the robotic arm using a dilator fixator, and each of the one or more subsequent dilators are configured to be positioned over the preceding dilators and increase the size of the working channel, wherein only the last added dilator is rigidly attached to the end effector; and the dilator fixator is mechanically coupled to the end effector by a bolt.

2. The robotic surgical system of claim 1, wherein each dilator except the last added dilator may be configured to be removed from the patient prior to performing a surgical procedure.

3. The robotic surgical system of claim 1, comprising a manipulator configured to adjust a position of the last added dilator during a surgical procedure without removing the last added dilator from the patient tissue.

4. The robotic surgical system of claim 3, wherein the manipulator is configured to aligning an axis of the last added dilator with a desired trajectory when adjusting the position of the last added dilator.

5. The robotic surgical system of claim 1, wherein each one or more subsequent dilators have a circumference larger than a circumference of the first dilator, and the one or more subsequent dilators increase the size of the working channel as each subsequent dilator is added.

6. The robotic surgical system of claim 1, comprising a surgical instrument guide configured to be placed inside of the attached dilator, wherein the surgical instrument guide is sized and shaped to fit at least partially inside the attached dilator along an axis defined by the dilator.

7. The robotic surgical system of claim 6, wherein the end effector is configured to hold and/or restrict movement of a surgical instrument therethrough.

8. The robotic surgical system of claim 7, wherein the surgical instrument comprises one or more of a drill bit, atap, a screwdriver, a screw, an implant, or an awl.

9. The robotic surgical system of claim 6, wherein the surgical instrument guide comprises one or more of a drill bit guide, a tap guide, a screwdriver guide, a screw guide, an awl guide, or an implant guide.

10. The robotic surgical system of claim 6, wherein the robotic arm is configured to be maneuvered to a desired position to align an axis defined by the surgical instrument guide at a desired trajectory in relation to the vertebrae of the patient.

11. The robotic surgical system of claim 1, wherein the system comprises:

a processor; and a memory storing instructions that, when executed by the processor, cause the processor to:

store a transformation between the patient's anatomy and one or more medical images;

determine an ideal implant trajectory; and provide, for display on a graphical user interface, the ideal implant trajectory for review by the surgeon.

12. The robotic surgical system of claim 11, wherein, if the surgeon agrees with the ideal implant trajectory, the system is configured to receive a surgeon input acknowledging the ideal implant trajectory at the graphical user interface, causing the ideal implant trajectory to be stored as the desired trajectory.

13. The robotic surgical system of claim 11, wherein, if the surgeon does not agree with the ideal implant trajectory, the system is configured to receive a surgeon input adjusting the ideal implant trajectory at the graphical user interface to generate an adjusted implant trajectory, causing the adjusted implant trajectory to be stored as the desired trajectory.

* * * * *